(12) United States Patent
Koike et al.

(10) Patent No.: US 11,906,356 B2
(45) Date of Patent: Feb. 20, 2024

(54) SPECTRAL-CHARACTERISTIC ACQUISITION APPARATUS AND METHOD OF OBTAINING SPECTRAL CHARACTERISTICS

(71) Applicants: Toshio Koike, Tokyo (JP); Nobuo Kikuchi, Saitama (JP); Dan Ozasa, Kanagawa (JP); Kohei Shimbo, Kanagawa (JP)

(72) Inventors: Toshio Koike, Tokyo (JP); Nobuo Kikuchi, Saitama (JP); Dan Ozasa, Kanagawa (JP); Kohei Shimbo, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 17/876,087

(22) Filed: Jul. 28, 2022

(65) Prior Publication Data

US 2023/0106354 A1 Apr. 6, 2023

(30) Foreign Application Priority Data

Sep. 30, 2021 (JP) ................. 2021-162364

(51) Int. Cl.
*G01J 3/02* (2006.01)
*G01N 21/25* (2006.01)
*G01N 33/34* (2006.01)

(52) U.S. Cl.
CPC ........... *G01J 3/0202* (2013.01); *G01J 3/0267* (2013.01); *G01N 21/251* (2013.01); *G01N 21/255* (2013.01); *G01N 33/346* (2013.01)

(58) Field of Classification Search
CPC .... G01J 3/0202; G01J 3/0267; G01N 21/251; G01N 21/255; G01N 33/346; H04N 1/00023; H04N 1/00588; H04N 1/00793
See application file for complete search history.

(56) References Cited

U.S. PATENT DOCUMENTS

| 4,874,161 A * | 10/1989 | Murasaki | B65H 43/00 |
| | | | 271/271 |
| 2003/0057639 A1* | 3/2003 | Chapman | B65H 7/00 |
| | | | 271/270 |

(Continued)

FOREIGN PATENT DOCUMENTS

| EP | 3712705 A1 | 9/2020 |
| JP | 2012-088085 | 5/2012 |
| JP | 2020-153814 | 9/2020 |

OTHER PUBLICATIONS

Extended European Search Report dated Dec. 5, 2022 issued in corresponding European Appln. No. 22186998.5.

*Primary Examiner* — Michael A Lyons
*Assistant Examiner* — Omar H Nixon
(74) *Attorney, Agent, or Firm* — Harness, Dickey & Pierce, P.L.C.

(57) ABSTRACT

A spectral-characteristic acquisition apparatus and a method of obtaining spectral characteristics. The spectral-characteristic acquisition apparatus includes a conveyor including a first conveyance roller pair disposed in a conveyance direction in which an object is conveyed and a second conveyance roller pair disposed downstream from the first conveyance roller pair in the conveyance direction, a sensor to detect that the object has reached the second conveyance roller pair, circuitry to control the second conveyance roller pair to drive by a predetermined amount with a driving force greater than a driving force of the first conveyance roller pair upon detecting that the object has reached the second conveyance roller pair by the sensor and to stop driving, and a color data obtainer to obtain color data from the object at a position where the object stops moving. In the spectral-characteristic acquisition apparatus, the circuitry estimates a spectral characteristic of the object.

20 Claims, 13 Drawing Sheets

(56) References Cited

U.S. PATENT DOCUMENTS

| | | |
|---|---|---|
| 2010/0225983 A1 | 9/2010 | Fujii et al. |
| 2014/0112687 A1 | 4/2014 | Ohmura et al. |
| 2015/0078788 A1 | 3/2015 | Koike et al. |
| 2015/0139671 A1 | 5/2015 | Matsumoto et al. |
| 2015/0227086 A1 | 8/2015 | Kondoh et al. |
| 2015/0338824 A1 | 11/2015 | Shimizu et al. |
| 2016/0026113 A1 | 1/2016 | Takahashi et al. |
| 2016/0223946 A1 | 8/2016 | Kikuchi et al. |
| 2016/0366296 A1 | 12/2016 | Isokawa |
| 2017/0227922 A1 | 8/2017 | Takami et al. |
| 2017/0248871 A1 | 8/2017 | Iwatsuki et al. |
| 2018/0321615 A1 | 11/2018 | Suzuki et al. |
| 2018/0329358 A1 | 11/2018 | Takami et al. |
| 2018/0335721 A1 | 11/2018 | Koike et al. |
| 2019/0204775 A1 | 7/2019 | Takami et al. |
| 2019/0212668 A1 | 7/2019 | Koike et al. |
| 2019/0219951 A1 | 7/2019 | Koike et al. |
| 2019/0227479 A1 | 7/2019 | Suzuki et al. |
| 2019/0238717 A1 | 8/2019 | Inage et al. |
| 2019/0339642 A1 | 11/2019 | Takami et al. |
| 2020/0156890 A1* | 5/2020 | Takane .................. B65H 9/006 |
| 2020/0233371 A1 | 7/2020 | Takami et al. |
| 2020/0300701 A1 | 9/2020 | Taneda et al. |
| 2020/0324991 A1* | 10/2020 | Nakamura ............... B65H 3/06 |
| 2021/0018860 A1 | 1/2021 | Aso et al. |

\* cited by examiner

| SPECTRAL SENSOR / COLOR CHART | $80_1$ | $80_2$ | $80_3$ | . | . | . |
|---|---|---|---|---|---|---|
| A | L*a*b*... | L*a*b*... | L*a*b*... | . | . | . |
| B | L*a*b*... | L*a*b*... | L*a*b*... | . | . | . |
| C | L*a*b*... | L*a*b*... | L*a*b*... | . | . | . |
| . | . | . | . | . | . | . |
| . | . | . | . | . | . | . |
| . | . | . | . | . | . | . |
| . | . | . | . | . | . | . |

SPECTRAL-CHARACTERISTIC ACQUISITION APPARATUS AND METHOD OF OBTAINING SPECTRAL CHARACTERISTICS

CROSS-REFERENCE TO RELATED APPLICATION

This patent application is based on and claims priority pursuant to 35 U.S.C. § 119(a) to Japanese Patent Application No. 2021-162364, filed on Sep. 30, 2021, in the Japan Patent Office, the entire disclosure of which is hereby incorporated by reference herein.

BACKGROUND

Technical Field

Embodiments of the present disclosure relate to a spectral-characteristic acquisition apparatus and a method of obtaining spectral characteristics.

Background Art

In the related art, some technologies have been proposed that obtain the spectral characteristics of the image of an object such as a recording medium to enhance the color reproduction of an image in a spectral-characteristic acquisition apparatus such as a printer or a copier. Such a spectral-characteristic acquisition apparatus includes a sheet conveyor that conveys an object such as a recording medium, and measures the colors of an image in a measurable area at a destination of conveyance of the object to obtain the spectral characteristics of the object.

Moreover, some technologies have been proposed that measure the color of an image with a high degree of precision. For example, a configuration or structure has been proposed that reverses the direction of rotation of a first sheet conveyance roller while stopping the rotation of a second sheet conveyance roller arranged downstream from the first sheet conveyance roller. Due to such a configuration or structure, the sheet can be in full contact with a reference plane for measurement.

However, the tension that is applied to the recording medium or the like varies depending on the sheet type or the thickness of the recording medium. For this reason, when a conventional method in the related art is employed and conditions such as the sheet type and thickness of the recording medium vary, the stop position of the measurable area tends to be shifted.

SUMMARY

Embodiments of the present disclosure described herein provide a spectral-characteristic acquisition apparatus and a method of obtaining spectral characteristics. The spectral-characteristic acquisition apparatus includes a conveyor including a first conveyance roller pair disposed in a conveyance direction in which an object is conveyed and a second conveyance roller pair disposed downstream from the first conveyance roller pair in the conveyance direction, a sensor to detect that the object has reached the second conveyance roller pair, circuitry to control the second conveyance roller pair to drive by a predetermined amount with a driving force greater than a driving force of the first conveyance roller pair upon detecting that the object has reached the second conveyance roller pair by the sensor and to stop driving, and a color data obtainer to obtain color data from the object at a position where the object stops moving. In the spectral-characteristic acquisition apparatus, the circuitry estimates a spectral characteristic of the object based on the color data obtained by the color data obtainer. The method includes conveying an object from a first conveyance roller pair arranged in a conveyance direction to a second conveyance roller pair arranged downstream from the first conveyance roller pair in the conveyance direction, detecting that the object has reached the second conveyance roller pair, driving the second conveyance roller pair by a predetermined amount with a driving force greater than a driving force of the first conveyance roller pair upon detecting that the object has reached the second conveyance roller pair, and stopping the second conveyance roller pair, obtaining color data from the object at a position where the second conveyance roller pair is stopped, and estimating a spectral characteristic of the object based on the color data obtained in the obtaining.

BRIEF DESCRIPTION OF THE DRAWINGS

A more complete appreciation of embodiments and the many attendant advantages thereof will be readily obtained as the same becomes better understood by reference to the following detailed description when considered in connection with the accompanying drawings.

Figure 1:
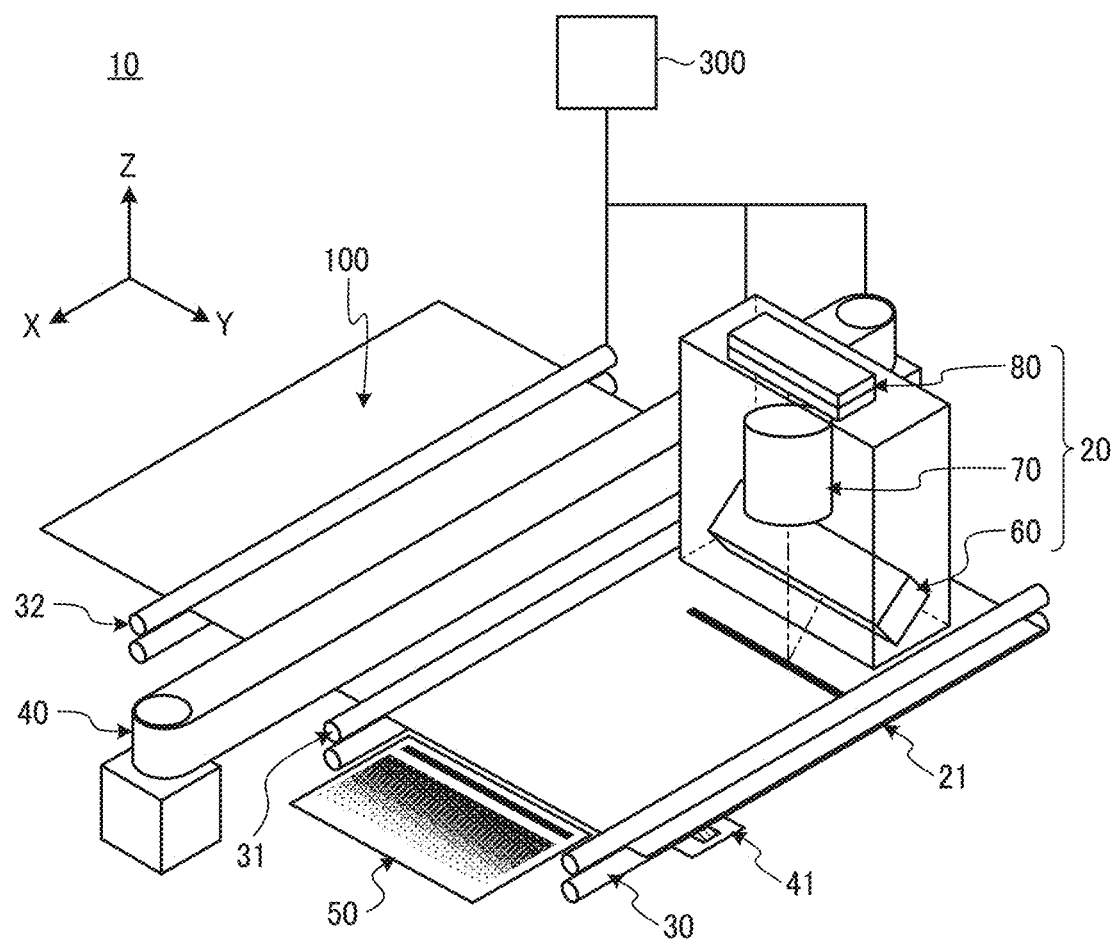
FIG. 1 is a block diagram illustrating an overall configuration of a printing system according to a first embodiment of the present disclosure.

The accompanying drawings are intended to depict embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present disclosure. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the present disclosure is not intended to be limited to the specific terminology so selected and it is to be understood that each specific element includes all technical equivalents that have the same structure, operate in a similar manner, and achieve a similar result.

A spectral-characteristic acquisition apparatus and a method of acquiring a spectral characteristic according to an embodiment of the present disclosure are described below in detail with reference to the accompanying drawings.

In the description of embodiments of the present disclosure given below, an object from which its spectral characteristics are obtained is an image-carrying medium such as a sheet of paper, and the object from which the spectral characteristics are obtained is referred to simply as the sheet. In the following description, unless otherwise specified, an X-axis direction indicates the width direction of a sheet, a Y-axis direction indicates the direction in which the sheet is conveyed, and a Z-axis direction indicates a direction orthogonal to an X-Y plane. In the present embodiment, the X-axis direction indicates a direction intersecting with the conveyance direction, and the Y-axis direction indicates the conveyance direction. The terms such as image formation," "recording," "printing," "image printing," and "fabricating" used herein may be used synonymously with each other.

First Embodiment

Firstly, a first embodiment of the present disclosure is described below with reference to accompanying drawings.

FIG. 1 is a perspective view of a configuration of a spectral-characteristic acquisition apparatus 10 according to the first embodiment of the present disclosure.

Figure 2:
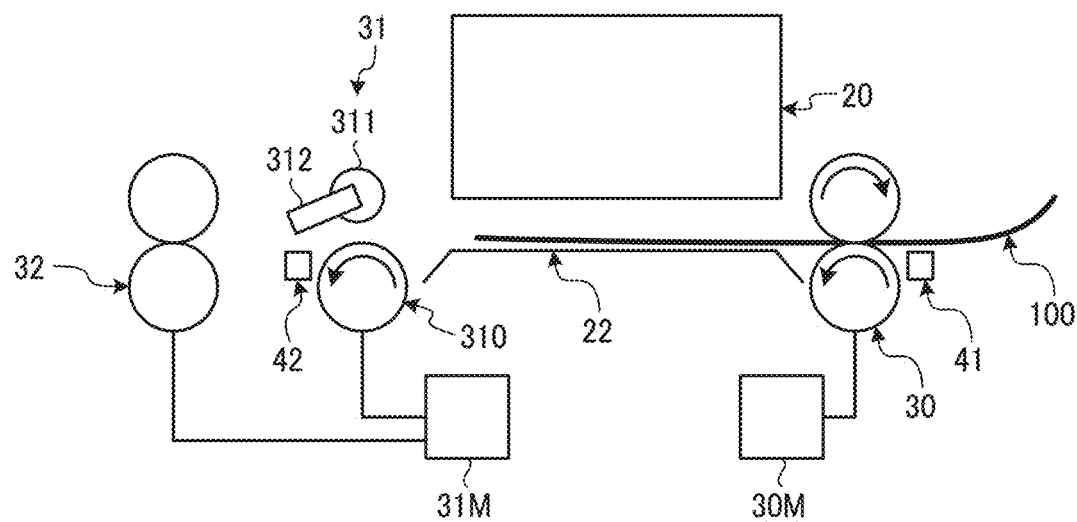
FIG. 2 is a diagram illustrating a configuration or structure around a conveyance unit, according to an embodiment of the present disclosure.

As illustrated in FIG. 1 and FIG. 2, the spectral-characteristic acquisition apparatus 10 according to the present embodiment includes a color data obtainer 20, a plurality of sheet conveyors 30, 31, and 32, a pair of sheet sensors 41 and 42, a color data obtainer conveyor 40, color charts for correction 50, and a controller 300. The color data obtainer 20 according to the present embodiment includes a linear light source 60, a reduction imaging lens 70, and a spectroscopic unit 80. The sheet conveyor 30, the sheet conveyor 31, and the sheet conveyor 32 according to the present embodiment serve as a conveyance unit, and the color data obtainer conveyor 40 according to the present embodiment serves as a second conveyance unit. The controller 300 according to the present embodiment serves as a controller.

The sheet 100 is conveyed in the Y-axis direction at a constant speed by the sheet conveyor 30, the sheet conveyor 31, and the sheet conveyor 32. The use of terms "upstream" and "downstream" are described and defined as follows. The direction in which the sheet 100 is conveyed is defined as a direction from an upstream portion of a color-data acquisition area 21 to a downstream portion of the color-data acquisition area 21. In FIG. 1, the sheet 100 is conveyed in the −Y-axis direction. Accordingly, an upstream portion of the color-data acquisition area 21 in the conveyance direction is located in the +Y-axis direction, and a downstream portion of the color-data acquisition area 21 in the conveyance direction is located in the −Y-axis direction. For example, in view of the sheet conveyor 30 and the sheet conveyor 31, the sheet conveyor 30 is arranged at an upstream portion of the color-data acquisition area 21 in the conveyance direction, and the sheet conveyor 31 is arranged at a downstream portion of the color-data acquisition area 21 in the conveyance direction. In view of the sheet sensor 41 and the sheet conveyor 30, the sheet sensor 41 is arranged at an upstream portion of the color-data acquisition area 21. In the following description, the terms "upstream" and "downstream" are used in view of the definition as described above.

The sheet conveyor 30, the sheet conveyor 31, and the sheet conveyor 32 are described below in detail. A printed sheet from which its color data is to be obtained has a significant impact on the performance of conveyance due to the differences in the thickness of the sheet or the differences in surface properties depending on, for example, the coating or image on the sheet. For example, the frictional resistance of the surface of a coated sheet is small In such cases, for example, a conveyance roller may skid, and the amount of conveyance of the sheet may become smaller than a desired amount of conveyance. It is effective to stably feed the sheet 100 to the color-data acquisition area 21 by preventing the sheet 100 from going further than intended from a desired position or by preventing the sheet 100 from failing to reach the desired position due to the insufficient amount of conveyance.

FIG. 2 is a diagram illustrating the configuration or structure around the sheet conveyor 30, the sheet conveyor 31, and the sheet conveyor 32, according to the present embodiment.

Each one of the sheet conveyor 30, the sheet conveyor 31, and the sheet conveyor 32 is composed of, for example, a drive roller and a driven roller, and each one of the rollers is made of a nip roll having grip or adhesion. Each of the sheet conveyor 30, the sheet conveyor 31, and the sheet conveyor 32 conveys the sheet 100 at a constant speed while nipping the sheet 100 between the drive roller and the driven roller. Among these conveyors, the sheet conveyor 31 according to the present embodiment is controlled in the color-data acquisition area 21 together with the sheet conveyor 30, and has a function to smooth out the wrinkles of the sheet 100. The drive roller and the driven roller of the sheet conveyor 30 according to the present embodiment serve as a first conveyance roller pair. The drive roller and the driven roller of the sheet conveyor 31 according to the present embodiment serve as a second conveyance roller pair.

The sheet conveyor 31 according to the present embodiment has an arm 312 used to move a roller 311 that is a driven roller. The arm 312 according to the present embodiment serves as a pressurizer that presses the roller 311 against the roller 310 that serves as a drive roller to apply pressure to the sheet 100. The sheet conveyor 31 moves the arm 312 to press the roller 311 against the roller 310. By so doing, each one of the roller 310 and the roller 311 can rotate while nipping the sheet 100 with a certain level of force. The controller 300 according to the present embodiment drives the roller 310 of the sheet conveyor 31 by a predetermined amount with a driving force greater than the driving force of the drive roller of the sheet conveyor 30, and then stops driving the roller 310 of the sheet conveyor 31. By so doing, the slack and wrinkles of the sheet 100 can be smoothed out.

The sheet conveyor 30 and the sheet conveyor 31 are coupled to a drive motor 30M and a drive motor 31M, respectively. The sheet conveyor 32 may be coupled to the drive motor 31M of the sheet conveyor 31. When the function to smooth out the slack or wrinkles of the sheet 100 is performed, the conveyance is performed upon making the driving force of the drive motor 31M for driving the roller 310 higher than the driving force of the drive motor 30M for driving the drive roller of the sheet conveyor 30.

In other words, the sheet conveyor 31 that is located at the downstream portion of the color-data acquisition area 21 in the conveyance direction feeds the sheet 100 to the downstream portion of the color-data acquisition area 21 while firmly pressing and sandwiching the sheet 100 with the arm 312, and the sheet conveyor 30 that is located at the upstream portion of the color-data acquisition area 21 in the conveyance direction rotates to apply load to the sheet 100 in the conveyance direction due to the driving force smaller than that of the sheet conveyor 31 on the downstream portion of the color-data acquisition area 21. Due to such control as described above, the force to feed the sheet 100 in the conveyance direction by the sheet conveyor 31 on the downstream portion of the color-data acquisition area 21 and the force that applies a load to the sheet 100 by the sheet conveyor 30 on the upstream portion of the color-data acquisition area 21 act to such an extent that the slack and wrinkles of the sheet 100 can be smoothed out.

The sheet conveyor 30 that is arranged at an upstream portion of the color-data acquisition area 21 in the conveyance direction can perform contrarotation in addition to the normal rotation.

The spectral-characteristic acquisition apparatus 10 includes a sheet sensor 41 and a sheet sensor 42. The sheet sensor 41 detects that the leading end of the sheet 100 has been conveyed to the sheet conveyor 30 arranged at an upstream portion of the color-data acquisition area 21 in the conveyance direction. The sheet sensor 42 serves as a sensor and detects that the leading end of the sheet 100 has been conveyed to and has reached the sheet conveyor 31 arranged at a downstream portion of the color-data acquisition area 21 in the conveyance direction.

For example, the sheet sensor 41 and the sheet sensor 42 irradiate the sheet 100 with light and detect the reflected light with, for example, a photodiode. Based on the output from the sheet sensor 41 and the sheet sensor 42, it is detected that the sheet 100 is at the position of the color-data acquisition area 21 implemented by the color data obtainer 20.

As illustrated in FIG. 2, a reference plane for measurement 22 is arranged under the bottom face of the color-data acquisition area 21. The reference plane for measurement 22 covers the area in which the color-data acquisition area 21 is moved in the X-direction by the color data obtainer conveyor 40, and is arranged so as to be in full contact with the sheet 100.

The reference plane for measurement 22 is made of, for example, a wide guide plate formed by painting a sheet metal in white or black. The color of such a painting has varying conditions for different purposes, and the reference plane for measurement 22 is replaceable. For example, the color of such painting is to be black in the case of use in conformity with the International Organization for Standardization (ISO) or when the reference plane for measurement 22 is used to calibrate the printing machine, and the color of such painting is to be white when a color profile for printing is to be generated.

Return to FIG. 1. As illustrated in FIG. 1, the color data obtainer conveyor 40 conveys the color data obtainer 20 in the width direction of the sheet 100. The color data obtainer conveyor 40 is, for example, a conveyance stage composed of, for example, a ball screw and a guide.

The color charts for correction 50 according to the present embodiment are used to correct the transformation matrix that is used to compute the spectral characteristics. The color charts for correction 50 will be described below in detail.

The spectral-characteristic acquisition apparatus 10 can simultaneously acquire spectral characteristics at a plurality of positions in the Y-axis direction in the color-data acquisition area 21 of the sheet 100.

The linear light source 60 irradiates the color-data acquisition area 21 with the linear light in a direction inclined by about 45 degrees with respect to a normal to the sheet 100. Further, the linear light source 60 illuminates an appropriate area with respect to the color-data acquisition area 21 such that reflected light from an area other than the color-data acquisition area 21 in the sheet 100 does not enter the spectroscopic unit 80.

As the linear light source 60, for example, an array of white light-emitting diodes (LEDs) that have radiation intensity for about the entire range of visible light may be used. However, no limitation is intended thereby, and a fluorescent lamp or a lamp light source such as a cold-cathode tube may be used as the linear light source 60.

It is desired that the linear light source 60 emit light in a wavelength range used for the spectral operation. Moreover, it is desired that the linear light source 60 can evenly irradiate all over the color-data acquisition area 21 with light. A collimator lens that concentrates the light emitted from the linear light source 60 and irradiates the sheet 100 with parallel light or converging light may additionally be arranged around such a linear light source.

The reduction imaging lens 70 according to the present embodiment is disposed such that the optical axis thereof will be parallel to a normal to the sheet 100, and has a function to form an image of the light beam reflected by the sheet 100 on the incident plane of the spectroscopic unit 80 with a prescribed magnifying power. In the present embodiment, the image-side telecentric characteristics are added to the reduction imaging lens 70. By so doing, the main light beam of the light flux incident on the imaging plane becomes approximately parallel to the optical axis. The reduction imaging lens 70 may be composed of a plurality of lenses.

By adding the image-side telecentric characteristics to the reduction imaging lens 70, the main light beam of the light flux incident on the imaging plane can easily be made approximately parallel to the optical axis. However, it is not always necessary to add the image-side telecentric characteristics to the reduction imaging lens 70. In such cases, similar advantageous effects can be achieved by adjusting, for example, the relative positions of each pinhole of a pinhole array 81 and each lens of a lens array 82, which will be described later in detail, according to the inclination of the main light beam at varying positions of the imaging plane.

The spectroscopic unit 80 has a function to distribute the diffuse reflection light of the light emitted to the sheet 100 and a function to output a signal in response to the reception of the distributed light. The spectroscopic unit 80 according to the present embodiment will be described later in detail with reference to FIG. 3.

The optical system as illustrated in FIG. 1 is a so-called 45/0 optical system in which the illumination light emitted from the linear light source 60 is incident on the sheet 100 at approximately 45 degrees and the spectroscopic unit 80 receives the light diffusely reflected by the sheet 100 in the vertical direction. However, the configuration or structure of the optical system according to the present embodiment is not limited to the one as illustrated in FIG. 1. For example, the optical system according to the present embodiment may be a so-called 0/45 optical system in which the illumination light emitted from the linear light source 60 is incident on the sheet 100 at 90 degrees and the spectroscopic unit 80 receives the light diffusely reflected by the sheet 100 at 45 degrees.

The configuration or structure of the spectroscopic unit 80 is described below with reference to FIG. 3.

Figure 3:
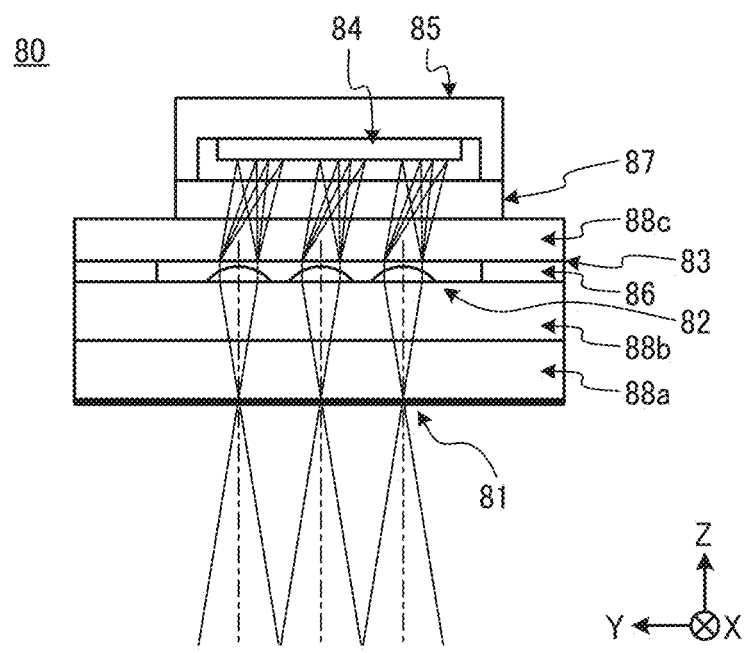
FIG. 3 is a cross-sectional view of a spectroscopic unit provided for a spectral-characteristic acquisition apparatus according to an embodiment of the present disclosure.

FIG. 3 is a cross-sectional view of the spectroscopic unit 80 provided for the spectral-characteristic acquisition apparatus 10 according to the present embodiment, and illustrates a part of a cross section parallel to the YZ plane of the spectroscopic unit 80.

As illustrated in FIG. 3, the spectroscopic unit 80 according to the present embodiment includes the pinhole array 81, the lens array 82, a diffraction element 83, and an imaging device 84. Further, the spectroscopic unit 80 includes a package 85, a spacer 86, a cover glass 87, and a plurality of glass bases 88a, 88b, and 88c.

The pinhole array 81 has a plurality of pinholes that serve as openings through which the light reflected from the sheet 100 passes. The multiple pinholes according to the present embodiment are arranged in the Z-axis direction on the imaging plane where the image of the light incident from the reduction imaging lens 70 is formed, and are arrayed at equal distances in the Y-axis direction.

FIG. 3 illustrates an embodiment in which three pinholes are arranged in the Y-axis direction.

The pinhole array 81 is integrally arranged on the glass base 88a that is transparent and flat and serves as a frame with optical transparency. A thin metal film such as a film made of nickel is evaporatively deposited on a transparent glass base, and a plurality of openings that serve as a plurality of pinholes are arrayed. As a result, the pinhole array 81 is formed. The light flux of the light reflected by varying points of the color-data acquisition area 21 of the sheet 100 is extracted by the multiple pinholes provided for the pinhole array 81.

However, no limitation is intended thereby, and a slit array with a plurality of rectangular openings or an oblique slit array in which a plurality of rectangular slits are inclined with respect to the Y-axis direction may be adopted in place of the pinhole array 81.

On the other side of the face of the glass base 88a on which the light reflected by the sheet 100 is incident, a glass base 88b that is transparent and is shaped like a flat plate and serves as a light-transmitting frame is bonded face-to-face. On the other side of the glass base 88b that is not bonded to the glass base 88a, a plurality of lenses are arrayed at equal distances in the Y-axis direction. In the present embodiment described with reference to FIG. 3, three lenses are arranged in the Y-axis direction to form the lens array 82. Each one of the multiple lenses of the lens array 82 concentrates the light flux of multiple laser beams that have passed through the multiple pinholes of the pinhole array 81, and forms an image on the imaging device 84.

In the lens array 82, a plurality of lenses 82a are arranged in a line in the Y-axis direction, and the multiple lenses 82a of the lens array 82 have a function to transform the diffused light flux that has passed through the multiple openings of the pinhole array 81 into weakly diffused light flux.

The weakly diffused light flux is a diffused light flux closer to a parallel luminous flux than an incident diffused light flux. In other words, the diffused light flux is diffused to a smaller extent, that is, weakened as compared with the incident diffused light flux.

The lenses 82a constituting the lens array 82 are arranged at positions corresponding to the openings constituting the pinhole array 81, and the diameters of the multiple lenses 82a are set such that all the light transmitted through the openings enters the lenses SL. However, no limitation is indicated thereby, and the planar shape of the multiple lenses 82a is not necessarily circular.

In the present embodiment, the pinhole array 81 and the lens array 82 are disposed so as to have the glass base 88a and the glass base 88b therebetween. However, no limitation is intended thereby. The thicknesses of the glass base 88a and the glass base 88b are determined such that the optical-path length of the pinhole array 81 and the lens array 82 will be shorter than the object-side focal length of each one of the multiple lenses 82a of the lens array 82. In the lens array 82, it is desired that the portions other than the openings of the multiple lenses 82a are shielded from light in order to eliminate the stray light.

In the Z-axis direction, a glass base 88c that is transparent and flat and serves as a frame with optical transparency is arranged so as to face the lens array 82. The glass base 88b and the glass base 88c are bonded through a spacer 86.

The spacer 86 is a member that gives a certain gap or space between the glass base 88b and the glass base 88c, and is, for example, a member in which a plurality through holes are arranged as desired on the planar portion of a flat metallic plate. On the face of the spacer 86 that faces the lens array 82, a portion of the spacer 86 that does not serve as a through-hole and a portion of the glass base 88*b* that does not have a lens are brought into contact with each other and bonded together.

On the surface of the spacer 86 facing the diffraction element 83, a portion of the spacer 86 that does not correspond to the through-hole and any desired portion of the 88*c* of the glass base are brought into contact with each other and bonded. Due to such a configuration, a certain gap or space is given between the glass base 88*b* and the glass base 88*c*. The through hole may be a small hole in which the multiple lenses of the lens array 82 can be accommodated, or may be a large hole in which a plurality of lenses are accommodated.

On the surface of the glass base 88*c* on which the light reflected by the sheet 100 is incident and that faces the lens array 82, a diffraction element 83 is arranged. The diffraction element 83 has a sawtooth shape formed at predetermined intervals on the glass base 88*c*, and serves as a diffraction grating that diffracts and spectrally distributes the incident light. The multiple bundles of light flux that have passed through the multiple lenses of the lens array 82 are spectrally separated by the diffraction element 83. On the imaging device 84, a plurality of diffraction patterns that correspond to the above multiple bundles of light flux are formed.

As the diffraction element 83 according to the present embodiment, it is desired that blazed grating whose diffraction efficiency of the primary diffracted light is enhanced be used. Using a blazed grating as the diffraction element 83 enables enhancement in the diffraction efficiency of only the primary diffracted light. As a result, the utilization efficiency of light in the optical system can be increased. Due to such a configuration, a signal of sufficient quality can be successfully obtained in a relatively short time, and the length of time required to obtain the spectral characteristics can be shortened.

The imaging device 84 is a line sensor in which a plurality of pixels are arranged in the Y-axis direction. The imaging device 84 uses a plurality of light-receiving elements arranged at different positions to receive the light of the multiple diffraction patterns formed by the lens array 82 and the diffraction element 83. By so doing, the radiation intensity of the incident light at a certain band of wavelength can be obtained. For example, a metal oxide semiconductor (MOS), a complementary metal-oxide-semiconductor (CMOS), and a charge-coupled device (CCD) may be used as the imaging device 84.

Figure 4:
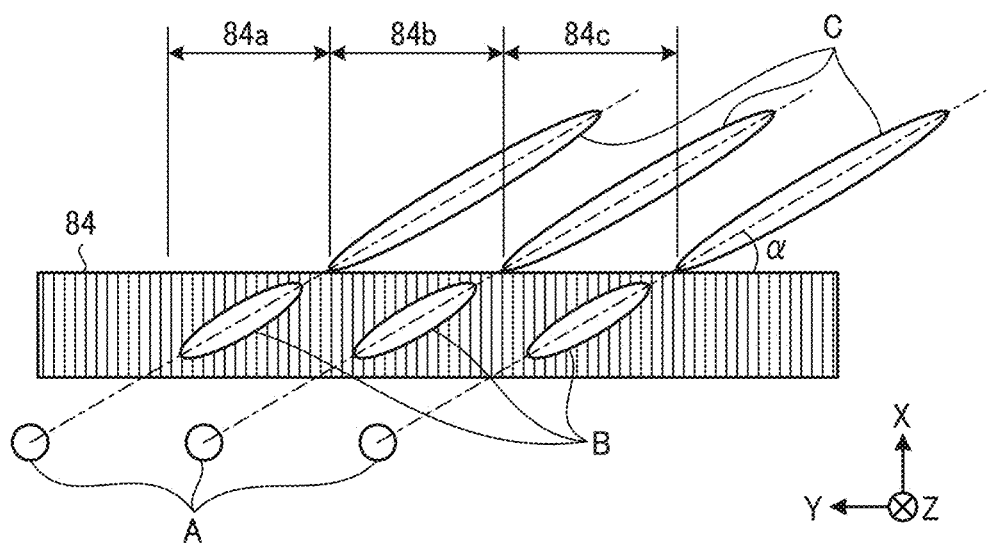
FIG. 4 is a diagram illustrating a plurality of diffraction patterns and how the light is received by an imaging device in a spectral-characteristic acquisition apparatus, according to an embodiment of the present disclosure.

FIG. 4 is a diagram illustrating a plurality of diffraction patterns A, B, and C and how the light is received by the imaging device 84 in the spectral-characteristic acquisition apparatus 10, according to the present embodiment.

The diffraction axis of the diffraction element 83 is inclined by an angle α with respect to the Y-axis direction. As illustrated in FIG. 4, a plurality of diffraction patterns A, B, and C are incident on the imaging device 84 with an angle α inclined with reference to the X-axis direction. In FIG. 4, three zero-order diffraction patterns A, thee+first-order diffraction patterns B, and three+second-order diffraction patterns C are arranged in line with each other in the Y-axis direction. Among those diffraction patterns, the first-order diffraction patterns B are to be received by the imaging device 84 in the arrangement. In FIG. 4, the three first-order diffraction patterns B that are formed by three lenses are received by the pixel area 84*a*, the pixel area 84*b*, and the pixel area 84*c* of the imaging device 84 and are converted into electrical signals. The electrical signal is output as the color data obtained by the spectroscopic unit 80.

As described above, in the spectral-characteristic acquisition apparatus 10 according to the present embodiment, the crosstalk of the multiple diffraction patterns is removed, and the spectral characteristic of the sheet 100 can be obtained based on the +primary diffraction pattern B. In the following description, the +primary diffraction pattern B may be referred to simply as a diffraction pattern.

The imaging device 84 according to the present embodiment is fixed inside the package 85, and the opening of the package 85 is covered with a transparent cover glass 87 that serves as a frame with optical transparency. The cover glass 87 is bonded to the side of the glass base 88*c* where the diffraction element 83 is not formed. One of the multiple pinholes of the pinhole array 81, one of the multiple lenses of the lens array 82 that corresponds to the above one pinhole, a portion of the diffraction element 83 through which the light flux from the above lens passes, and a portion of the rows of pixels of the imaging device 84 together serve as one optical spectroscope. Accordingly, a portion that has the function of one spectroscope may be referred to as a spectral sensor in the following description.

In FIG. 3 and FIG. 4, only three spectral sensors are illustrated for the sake of simplification. However, no limitation is intended thereby, and a configuration having a large number of spectroscopic sensors may be employed. For example, when the imaging device 84 that has one-thousand and twenty-four pixels are adopted and the number of pixels in the portion of the rows of pixels is set to ten, one-hundred two spectral sensors can be configured. Such spectral sensors are arranged in the Y-axis direction parallel to the conveyance direction of the sheet 100, and serve as a plurality of spectral sensors arranged in the conveyance direction of the object.

In the optical system for spectrometry that makes up the spectroscopic unit 80, the relative positional displacement between the imaging device 84 and the multiple diffraction patterns formed by the pinhole array 81, the lens array 82, and the diffraction element 83 has a great influence on the accuracy of the acquisition of the spectral characteristics. In the present embodiment, in order to control such positional displacements, the pinhole array 81, the lens array 82, the diffraction element 83, and the imaging device 84 are overlaid on top of each other in layers in the optical-axis direction of the reduction imaging lens 70 and bonded together in an integrated manner.

An outline of the controller 300 of the spectral-characteristic acquisition apparatus 10 is described below with reference to FIG. 5.

Figure 5:
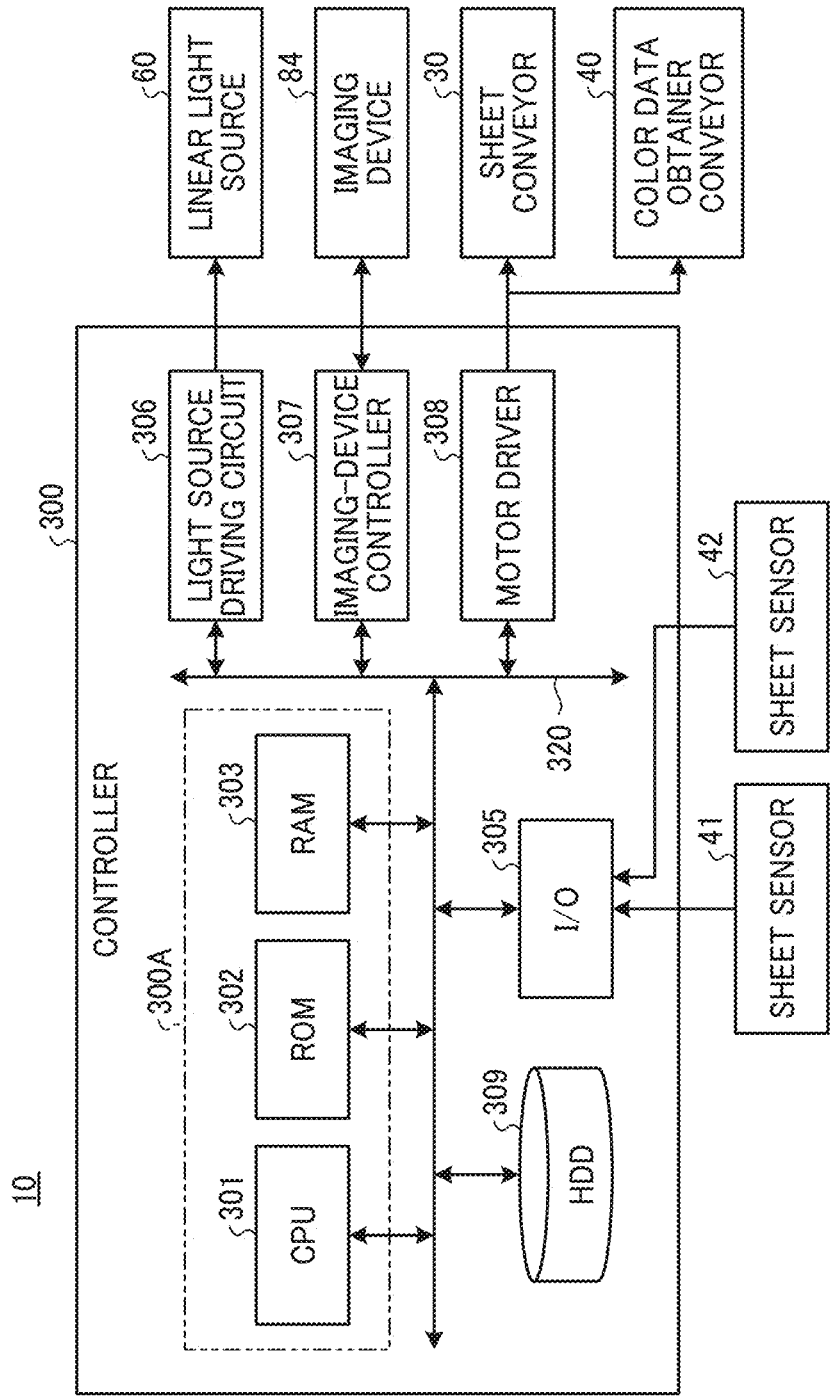
FIG. 5 is a block diagram of a hardware configuration of a spectral-characteristic acquisition apparatus according to an embodiment of the present disclosure.

FIG. 5 is a block diagram of a hardware configuration of the spectral-characteristic acquisition apparatus 10 according to the present embodiment.

The controller 300 according to the present embodiment includes a main controller 300A, an input and output (I/O) 305, a light source driving circuit 306, an imaging-device controller 307, a motor driver 308, and a hard disk drive (HDD) 309.

The main controller 300A according to the present embodiment includes a central processing unit (CPU) 301, a read-only memory (ROM) 302, and a random access memory (RAM) 303.

These elements of the main controller 300A are electrically coupled to each other through a system bus 320.

The CPU 301 controls the operation of the spectral characteristic acquisition apparatus 10 in a centralized manner. The CPU 301 uses the RAM 303 as a work area, and executes a program stored in the ROM 302 or the like to control all operations of the spectral-characteristic acquisition apparatus 10 and implement various kinds of functions as will be described later in detail. The HDD 309 stores, for example, the obtained color information.

The input and output (I/O) 305 receives, for example, the detection signal (ON signal) obtained by the sheet sensor 41 or the sheet sensor 42.

The light source driving circuit 306 is an electric circuit that outputs, based on the received control signal, a driving signal such as a driving voltage used to turn on the linear light source 60 to emit light.

The imaging-device controller 307 controls imaging by the imaging device 84 included in the spectroscopic unit 80 according to the input control signal. The image data that is captured by the imaging device 84 is sent to the HDD 309 as color data through the imaging-device controller 307 and stored therein.

The motor driver 308 is an electric circuit that outputs a driving signal such as a driving voltage to a plurality of motors that drive or operate a plurality of sheet conveyors 30, 31, and 32, and a color data obtainer conveyor 40 according to the input control signal. The multiple motors that drive the sheet conveyor 30, the sheet conveyor 31, and the sheet conveyor 32 to rotate include, for example, a motor that drives the arm 312 to move in addition to the drive motor 30M and the drive motor 31M that drive a plurality of drive rollers.

A method of controlling the sheet conveyor for conveying the sheet 100 in the Y-axis direction is described below.

The control in which the sheet 100 is detected by the sheet sensor 41 at an upstream portion of the color-data acquisition area 21 is similar to conventional control in the related art, and thus the description of such a control is omitted. A control method to be used when the sheet 100 is detected by the sheet sensor 42 at a downstream portion of the color-data acquisition area 21 is described below.

Figure 6A:
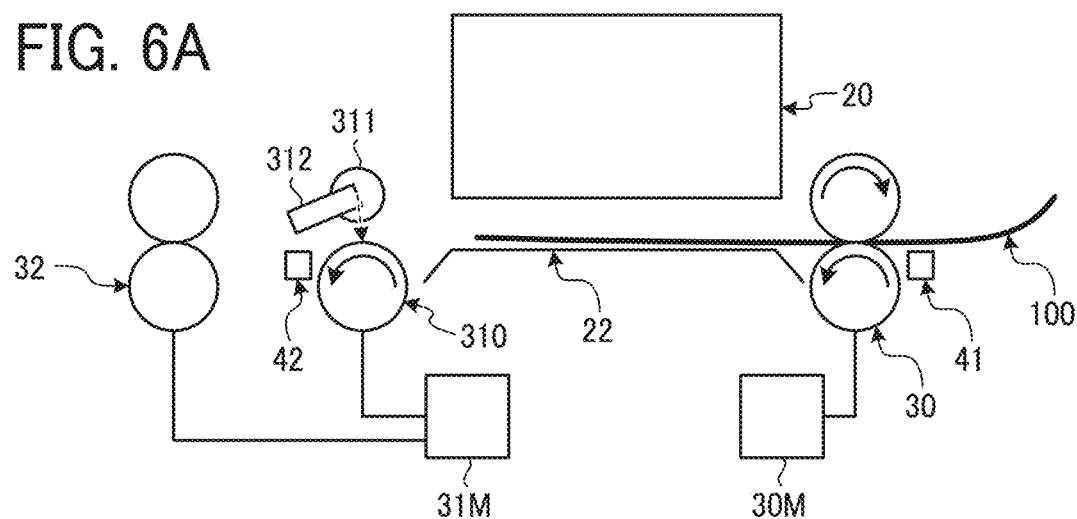
FIG. 6A, FIG. 6B, and FIG. 6C are schematic views of the operation of a plurality of sheet conveyors according to an embodiment of the present disclosure.
Figure 6B:
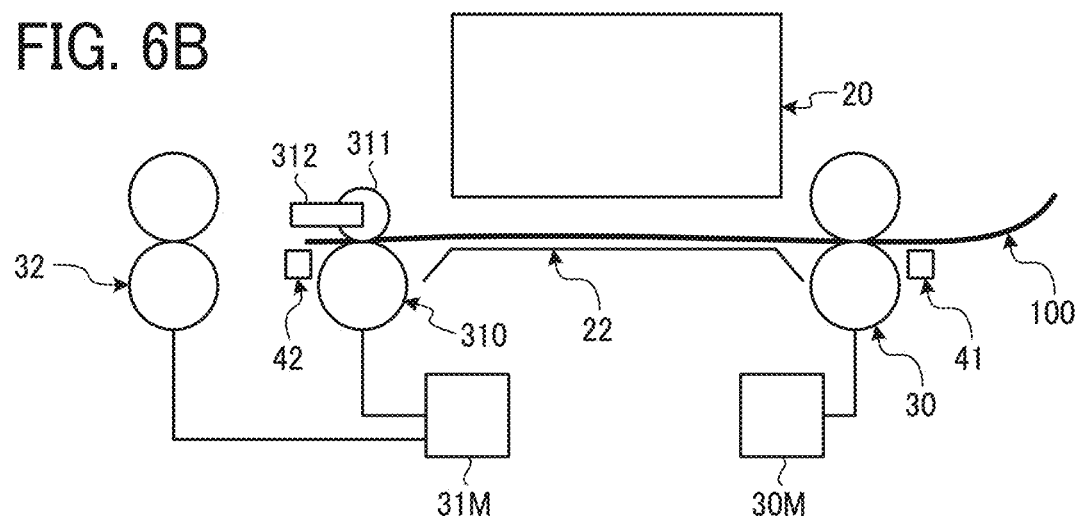
Figure 6C:
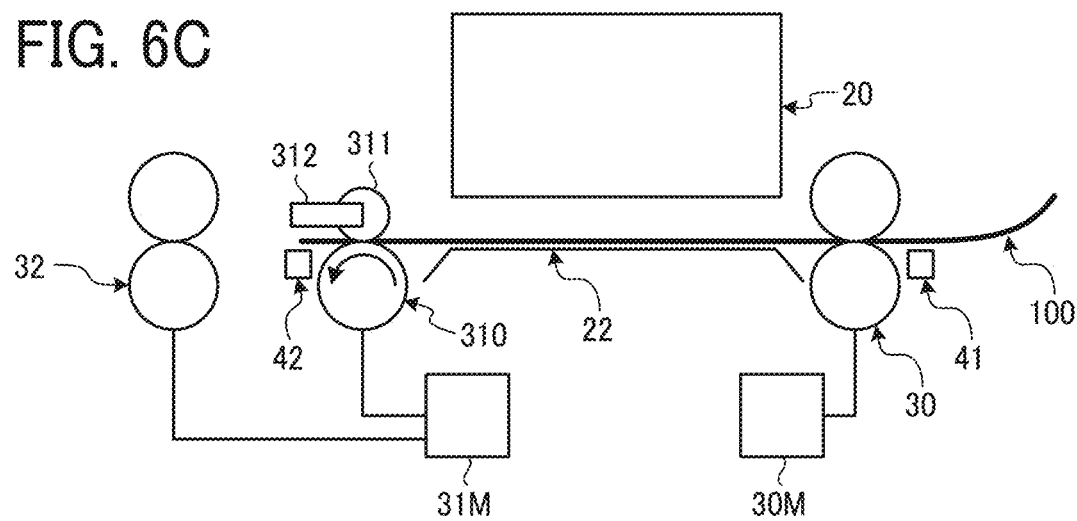

FIG. 6A, FIG. 6B, and FIG. 6C are schematic views of the operation of the sheet conveyor 30 and the sheet conveyor 31, according to the present embodiment.

Firstly, the controller 300 drives the drive rollers of the sheet conveyor 30 and the sheet conveyor 31 to convey the sheet 100 in the conveyance direction (see FIG. 6A).

Subsequently, when the sheet sensor 42 detects the leading end of the sheet 100, the controller 300 stops the conveyance of the sheet 100, and drives the arm 312 to press the roller 311 against the sheet 100 (see FIG. 6B). The timing at which the controller 300 stops the conveyance of the sheet 100 may be determined as desired. In the present embodiment, the conveyance of the sheet 100 is stopped as soon as the leading end of the sheet 100 is detected by the sheet sensor 42. However, no limitation is indicated thereby, and the sheet 100 may be stopped at a prescribed timing after the leading end of the sheet 100 is detected by the sheet sensor 42, depending on, for example, the relative positions of the sheet sensor 42 and the color-data acquisition area 21. As described above, due to the use of the sheet sensor 42, the sheet 100 can be stopped at the color-data acquisition area 21 with a high degree of precision, and the area of the sheet 100 at a downstream portion of the color-data acquisition area 21 can be firmly held by the arm 312.

Subsequently, the controller 300 operates the drive motor 31M by a predetermined amount in order to smooth out the slack or wrinkles of the sheet 100 (see FIG. 6C). When the drive motor 31M is operated by a predetermined amount, the driving force of the drive motor 30M is made smaller than that of the drive motor 31M. For example, the driving force of the drive motor 30M is set to 0. Alternatively, the driving force to the drive roller of the sheet conveyor 30 may be disengaged by a clutch. As the roller 310 of the sheet conveyor 31 on the downstream portion of the color-data acquisition area 21 rotates by a predetermined amount, the sheet 100 is fed by a predetermined amount in the conveyance direction with the rotation of the driven roller 311. The driving force of the sheet conveyor 30 at an upstream portion of the color-data acquisition area 21 is 0. Accordingly, when the sheet conveyor 31 at a downstream portion of the color-data acquisition area 21 sends out the sheet 100 in the conveyance direction, the slack, sag, or wrinkles of the sheet 100 are smoothed out. After that, even if the sheet 100 is under tension due to the load and the degree of tension reaches a predetermined value, the sheet conveyor 30 on the upstream portion of the color-data acquisition area 21 rotates as pulled by the sheet 100, or the sheet 100 is pulled by the sheet conveyor 30 on the upstream portion of the color-data acquisition area 21 in the conveyance direction. Accordingly, the damage to the sheet 100 can be reduced.

The amount of rotation of the roller 310 of the sheet conveyor 31 on the downstream portion of the color-data acquisition area 21 is controlled to such an extent that the slack and wrinkles of the sheet 100 can sufficiently be smoothed out, and is typically set to a few percent or less of the distance between the sheet conveyor 30 and the sheet conveyor 31.

With such control, the sheet 100 can be conveyed to a stable position of the color-data acquisition area 21, and color measurement can stably be performed as there is no slack, sag, or wrinkle. Further, the damage to the sheet 100 can be further reduced.

Figure 7A:
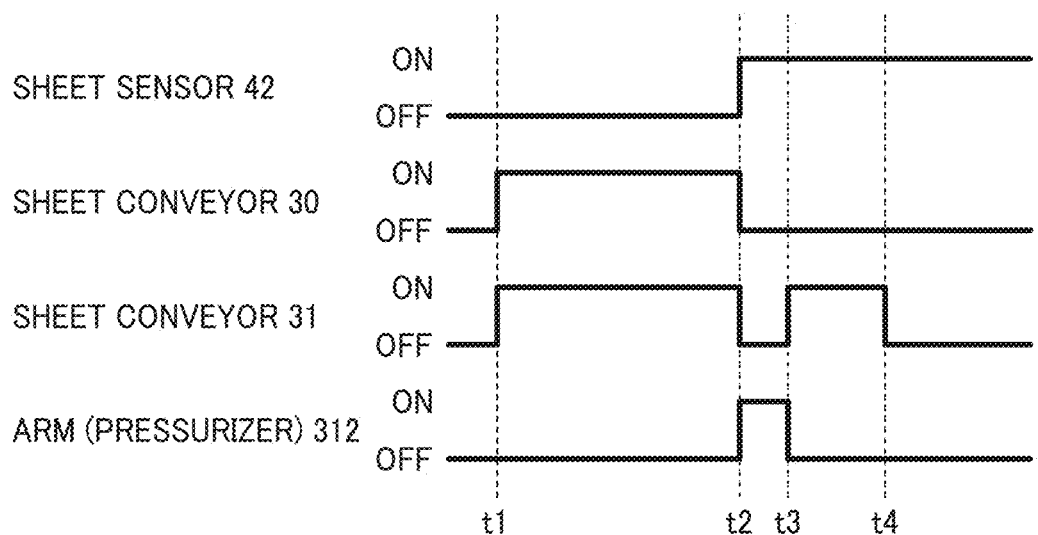
FIG. 7A and FIG. 7B are timing charts illustrating the timings at which a plurality of sheet conveyors are driven, according to an embodiment of the present disclosure.
Figure 7B:
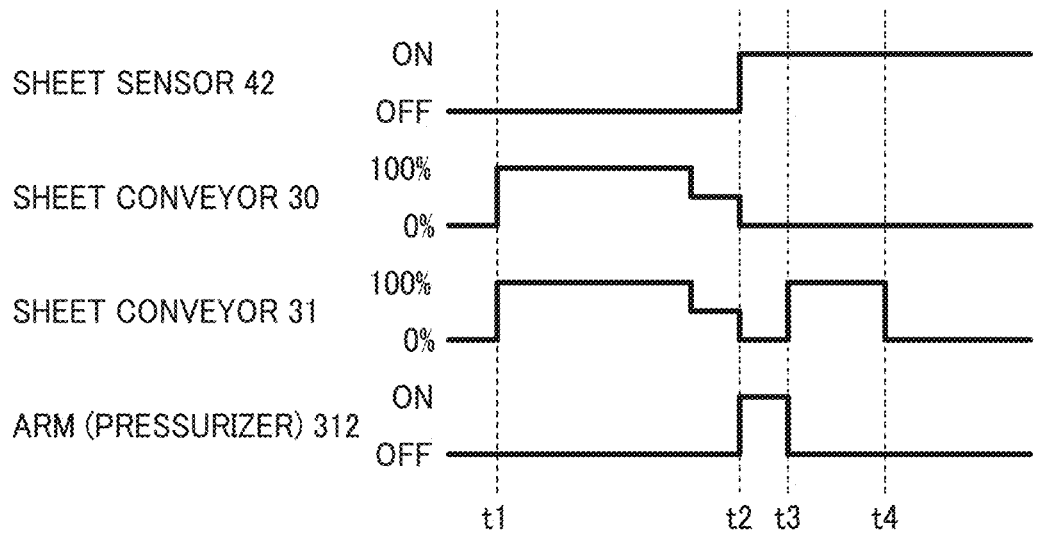

FIG. 7A and FIG. 7B are timing charts illustrating the timings at which the sheet conveyor 30 and the sheet conveyor 31 are driven, according to the present embodiment.

FIG. 7A is a timing chart illustrating the timing at which the sheet conveyor 30 and the sheet conveyor 31 are driven, according to the present embodiment.

As illustrated in FIG. 7A, the controller 300 turns on the operation of the sheet conveyor 31 and the sheet conveyor 32 at a timing t1 when the leading end of the sheet 100 is detected by the sheet sensor 41, and conveys the sheet 100 in the conveyance direction.

Subsequently, the controller 300 turns off the operation of both the sheet conveyor 30 and the sheet conveyor 31 at a timing t2 when the leading end of the sheet 100 is detected by the sheet sensor 42, and turns on the operation of the arm 312 that serves as a pressurizer.

After that, at a timing t3 when the arm 312 reaches a position where the sheet 100 is to be nipped, the controller 300 turns on the sheet conveyor 31.

Further, at the timing t3 when the arm 312 moves and reaches the position where the sheet 100 is to be nipped, the controller 300 turns on and drives the sheet conveyor 31 by a predetermined amount at a timing t4. It is assumed that the arm 312 is at a position to hold or nip the sheet 100 even after the timing t3.

After the timing t4, the controller 300 turns off the sheet conveyor 31 and reads the color data from the color-data acquisition area.

When a stepping motor is adopted as a motor for driving the sheet conveyor 30 and the sheet conveyor 31 and such a stepping motor is abruptly stopped at the stop position of the sheet 100, a large load may be placed and a step-out error may occur. In order to handle such a situation, the conveyance speed of the sheet 100 is reduced in advance from the first conveyance speed to the second conveyance speed at an upstream portion of the color-data acquisition area 21 before reaching the sheet sensor 42, and the stepping motor that is controlled to drive at the second conveyance speed is stopped as soon as the sheet sensor 42 is turned on. By so doing, the stepping motor can instantaneously be stopped at the stop position of the sheet 100. In order to decelerate the conveyance speed of the sheet 100 ahead of the sheet sensor 42, the conveyance speed of the sheet 100 may be reduced based on the estimated timing at which the sheet 100 is fed, or an additional sheet sensor may be arranged at a position where the speed of the sheet 100 is decelerated. Other desired methods may be adopted to decelerate the conveyance speed of the sheet 100 ahead of the sheet sensor 42.

FIG. 7B is a timing chart when the conveyance speed of the sheet 100 is reduced immediately before the sheet 100 reaches the sheet sensor 42, according to the present embodiment.

As illustrated in FIG. 7B, the controller 300 reduces the driving force of the sheet conveyor 31 and the sheet conveyor 30 from 100% immediately before the timing at which the sheet sensor 42 is turned on. By so doing, the conveyance speed is decreased from the first conveyance speed to the second conveyance speed. Then, the controller 300 turns off the sheet conveyor 30 and the sheet conveyor 31 to stop the stepping motor at the timing t2 where the conveyance speed is reduced to the second conveyance speed. The second conveyance speed is relatively slow but is not so slow as to cause a step-out failure. In the other respects, FIG. 7B is equivalent to FIG. 7A. The conveyance speed of the sheet 100 may be reduced immediately before the sheet sensor 42 step by step instead of being reduced at a time.

As described above, in the present embodiment, each one of the sheet conveyor 30 and the sheet conveyor 31 is coupled to a different drive motor. However, no limitation is intended thereby, and a clutch including an electromagnetic clutch or a gear including a reverse gear may be used, and the above operation may be performed by one drive motor.

Comparison Between Results of Implementation

The evaluation result that is obtained when the apparatus according to the above embodiments of the present disclosure is implemented is given below by way of example. As a first example of the apparatus according to the above embodiments of the present disclosure, the performance of conveyance of the sheet 100 was evaluated under the conditions given below.

First Example

In a first example of the present disclosure, the distance between the sheet conveyor 30 at an upstream portion of the color-data acquisition area 21 and the sheet conveyor 31 at a downstream portion of the color-data acquisition area 21 is 200 millimeters (mm). In the first example of the present disclosure, the linear velocity of the conveyors is 100 mm per second (sec).

First Control Sample

In a first control sample of the above example of the present disclosure, a control that is triggered by a feeding operation is performed as follows. When the sheet 100 is conveyed at a conveyance speed of 100 mm/sec and the distance of conveyance and the linear velocity per second of the sheet conveyor are 200 mm and 100 mm, respectively, the sheet 100 is stopped in 2 seconds (sec), which is obtained by dividing 200 mm by 100 mm.

Results of Comparison

For each one of the first example of the present disclosure and the first control sample of the above example of the present disclosure, the stop position of the sheet 100 at the sheet conveyor 31 at a downstream portion of the color-data acquisition area 21 was measured, and the amount of misalignment from the desired stop position of the sheet was measured. By way of example, the measurement was performed five times, and the average values of the amounts of misalignment were compared with each other. When the sheet 100 is at an upstream portion of the color-data acquisition area 21 than the desired position, the value is indicated with a minus sign.

First Table

| Brand | Sheet Type | Basis Weight (grams per square meter (gsm)) | Size | Amount of Misalignment from Desired Position (mm) | |
|---|---|---|---|---|---|
| | | | | First Example | First Control Sample |
| My Paper | Plain Paper | 67 | SRA3 | 0.2 | −3 |
| OK Top Coat+ | Coated Paper | 73.3 | SRA3 | 0.2 | −4 |
| OK Top Coat+ | Coated Paper | 127.9 | SRA3 | 0.2 | −4 |
| OK Special Art Post | Coated Paper | 279 | SRA3 | 0.5 | −6 |

In view of the results in the first table, it is understood from the first control sample of the above example of the present disclosure that the performance of conveyance of the sheet 100 is worse in the coated paper than in the plain paper and gets worse as the thickness of the sheet or paper is thicker. In order to handle such a situation, in the first example of the present disclosure, the conveyance of the sheet 100 is stopped as soon as the leading end of the sheet 100 is detected by the sheet sensor 42. Due to such a configuration, even when the conditions in, for example, the type of sheet change, the sheet 100 can be stopped at a stop position in the measurable area in a stable manner.

Return to FIG. 5. As illustrated in FIG. 5, the controller 300 can estimate and calculate the spectral characteristics of the sheet 100 using a transformation matrix based on the obtained color data. Some of or the entirety of these controlling functions of the CPU 301 may be implemented by an electronic circuit such as an application-specific integrated circuit (ASIC) and a field-programmable gate array (FPGA).

Figure 8:
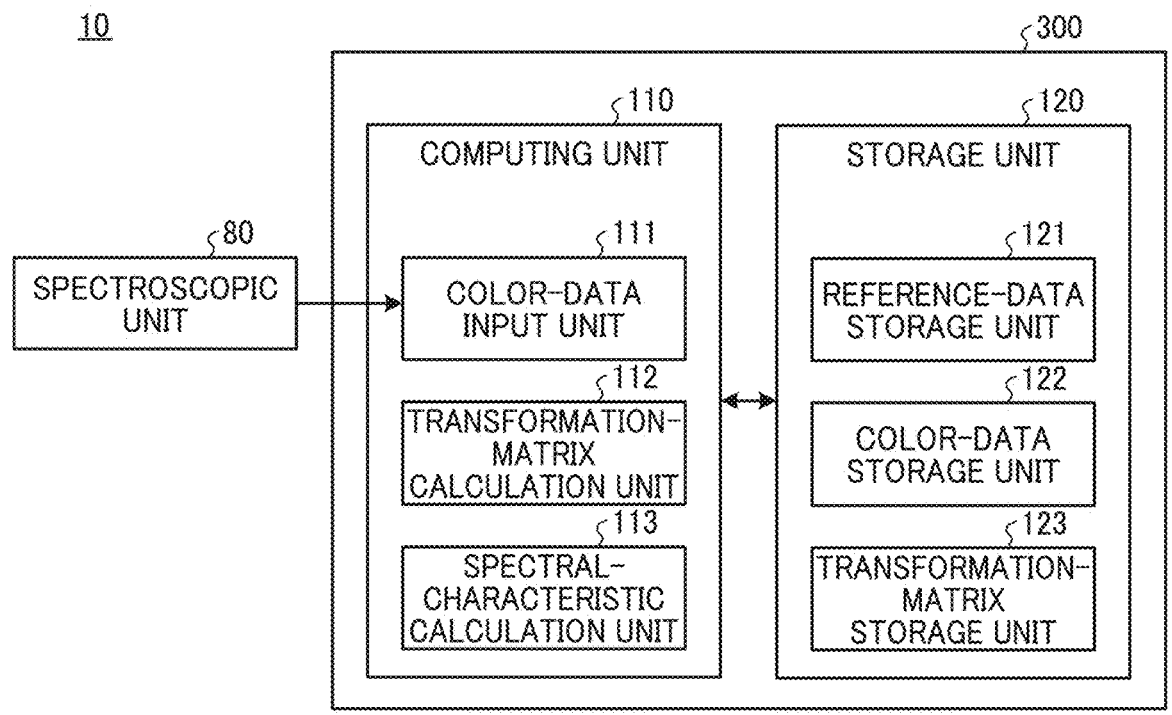
FIG. 8 is a block diagram illustrating a functional configuration used to estimate and calculate the spectral characteristics of a spectral-characteristic acquisition apparatus, according to an embodiment of the present disclosure.

FIG. 8 is a block diagram illustrating a functional configuration used to estimate and calculate the spectral characteristics of the spectral-characteristic acquisition apparatus 10, according to the present embodiment.

The controller 300 according to the present embodiment includes a computing unit 110 and a storage unit 120. The computing unit 110 includes a color-data input unit 111, a transformation-matrix calculation unit 112, and a spectral-characteristic computing unit 113. The storage unit 120 includes a reference-data storage unit 121, a color-data storage unit 122, and a transformation-matrix storage unit 123. The multiple functions of the computing unit 110 and a method of estimating and calculating the distribution of spectral reflectance as the spectral characteristics of the sheet 100 are described below.

Once the sheet 100 is irradiated with the light emitted from the linear light source 60 in the spectral-characteristic acquisition apparatus 10 according to the present embodiment, an electrical signal is output from the imaging device 84 of the spectroscopic unit 80 that has received the light of the diffraction patterns, and the output electrical signal is input to the color-data input unit 111 of the controller 300 as color data.

Once the color data is received, the spectral-characteristic computing unit 113 computes the spectral characteristic of the sheet 100 from the color data using the transformation matrix stored in advance in the transformation-matrix storage unit 123.

In the present embodiment, a method is described in which the spectral-characteristic computing unit 113 estimates and calculates, based on the color data obtained by one of the multiple spectral sensors provided for the spectroscopic unit 80, the distribution of spectral reflectance as the spectral characteristics of a sheet. The spectral characteristics may be determined by a method different from the method as will be described later in detail.

The color data vi, where i denotes one of the natural numbers 1 to N, is obtained from the N pixels that make up one of the multiple spectral sensors of the spectroscopic unit 80, and is stored in a matrix V. A matrix r that uses the matrix V and the transformation matrix G to store the spectral reflectance of varying wavelength bands such as thirty-one wavelength bands with a 10-nanometer (nm) pitch between 400 to 700 nm is expressed in a first equation given below. The transformation matrix G according to the present embodiment serves as a transformation matrix specified in advance.

$$r = Gv \qquad \text{First Equation}$$

As indicated by the second equation, the third equation, and the fourth equation given below, a method of least squares is used based on a matrix R that stores the distribution of the spectral reflectance of a plurality of reference samples such as n reference samples known in the art and a matrix V that stores the color data v of a reference sample obtained by the multiple optical sensors, and the transformation matrix G is obtained by minimizing the square norm$\| \ \|$ 2 of errors.

$$R = [r1, r2, \ldots, rn] \qquad \text{Second Equation}$$

$$V = [v1, v2 \ldots, vn] \qquad \text{Third Equation}$$

$$e = \|R - GV\|^2 \rightarrow \min \qquad \text{Fourth Equation}$$

The transformation matrix G that serves as a regression equation and obtains R using V, where V and R denote an explanatory variable and a target variable, respectively, can be obtained based on a fifth equation given below and, for example, the Moore-Penrose generalized inverse matrix with which the square of the minimum norm solution of matrix V can be obtained. In the fifth equation, the superscript T denotes the transpose of a matrix, and superscript −1 denotes the inverse matrix.

$$G = RVT(VV^T)^{-1} \qquad \text{Fifth Equation}$$

In the spectral-characteristic acquisition apparatus 10, the acquisition result of the spectral reflectance of the reference sample is stored in advance in the reference-data storage unit 121 of the controller 300.

The transformation-matrix calculation unit 112 generates the matrix Vref based on the color data obtained from the reference sample in the spectral-characteristic acquisition apparatus 10. Moreover, the transformation-matrix calculation unit 112 generates the matrix Rref from the spectral reflectance distribution of the reference sample stored in the reference-data storage unit 121. The transformation-matrix calculation unit 112 calculates the transformation matrix G from the matrices Vref and Rref generated as above based on the fifth equation.

The transformation matrix G that is calculated by the transformation-matrix calculation unit 112 as above is stored in the transformation-matrix storage unit 123. In the spectral-characteristic acquisition apparatus 10, the matrix Vref of the color data that is obtained from the reference sample is stored in the color-data storage unit 122 of the controller 300.

When the spectral characteristic of the sheet 100 is estimated, the spectral-characteristic computing unit 113 first generates the matrix Vexp from the color data of the sheet 100 and obtains the transformation matrix G stored in the transformation-matrix storage unit 123. The spectral-characteristic computing unit 113 can obtain the spectral characteristic Rexp of the sheet 100 by estimation based on the second equation using the matrix Vexp and the transformation matrix G.

In the above-described estimation and calculation, it is desired that a plurality of reference samples that are used for the calculation of the transformation matrix G be evenly selected from the color range or the color gamut that can be reproduced on a print image in the color space of, for example, an XYZ color system and a L*a*b* color system. By using the transformation matrix G that is calculated based on such reference samples as above, for example, the spectral characteristics of the image on the sheet 100 can be estimated with a high degree of precision.

However, the preparation, maintenance, and measurement of such reference samples require a large amount of time and cost. Accordingly, it is desired that the transformation matrix G be obtained based on a small number of reference samples within a range in which the estimation accuracy of the spectral characteristics can be maintained to a sufficient degree.

As an example of the multiple reference samples, a toner image can be used with the twenty-seven colors that are evenly selected from a color reproducible range of an electrophotographic image forming apparatus.

Figure 9:
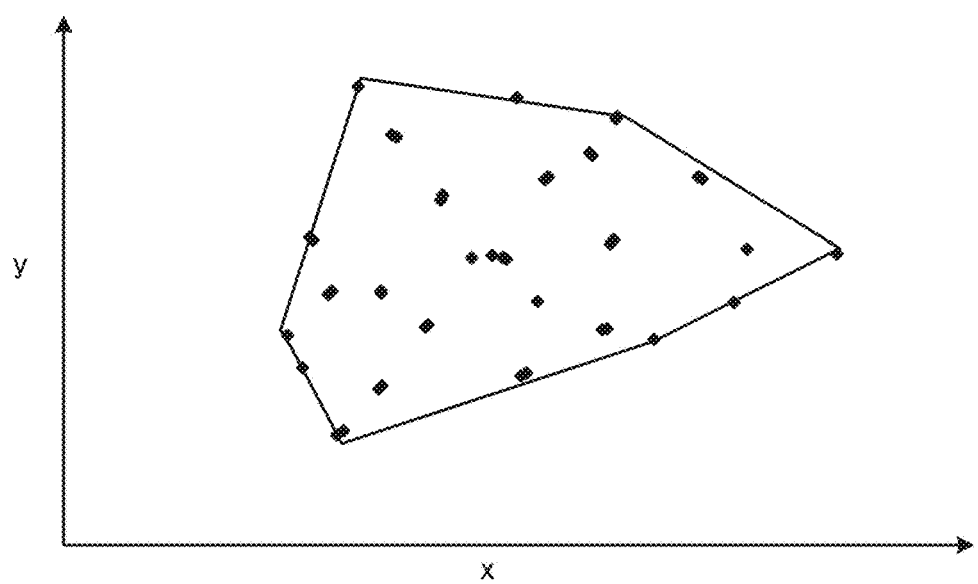
FIG. 9 is a diagram illustrating a distribution of the xy chromaticity of a plurality of reference samples and the range of color reproduction of a toner image, according to an embodiment of the present disclosure.

FIG. 9 illustrates the xy chromaticity of a plurality of reference samples of twenty-seven colors, according to the present embodiment.

Each point in FIG. 9 indicates the xy chromaticity of the multiple reference samples, and the solid lines in FIG. 9 indicate the range of color reproduction of a toner image. FIG. 9 illustrates that the reference samples are evenly selected from the color reproduction range of the toner image.

In the spectral-characteristic acquisition apparatus 10 according to the present embodiment, based on the reference samples as selected above the transformation matrix G that is calculated by the transformation-matrix calculation unit 112 as above is stored in advance in the transformation-matrix storage unit 123.

The operations of the color data obtainer 20 and the sheet 100 when the spectral-characteristic acquisition apparatus 10 obtains the color data are described below with reference to FIG. 10A, FIG. 10B, FIG. 10C, and FIG. 10D.

FIG. 10A, FIG. 10B, FIG. 10C, and FIG. 10D are plan views of the sheet 100 as viewed in the +Z-axis direction when the color data is being obtained, according to the present embodiment.

FIG. 10A, FIG. 10B, FIG. 10C, and FIG. 10D are diagrams each illustrating the sheet 100 being conveyed in the −Y-axis direction indicated by an arrow of the reference plane for measurement 22.

Figure 10:
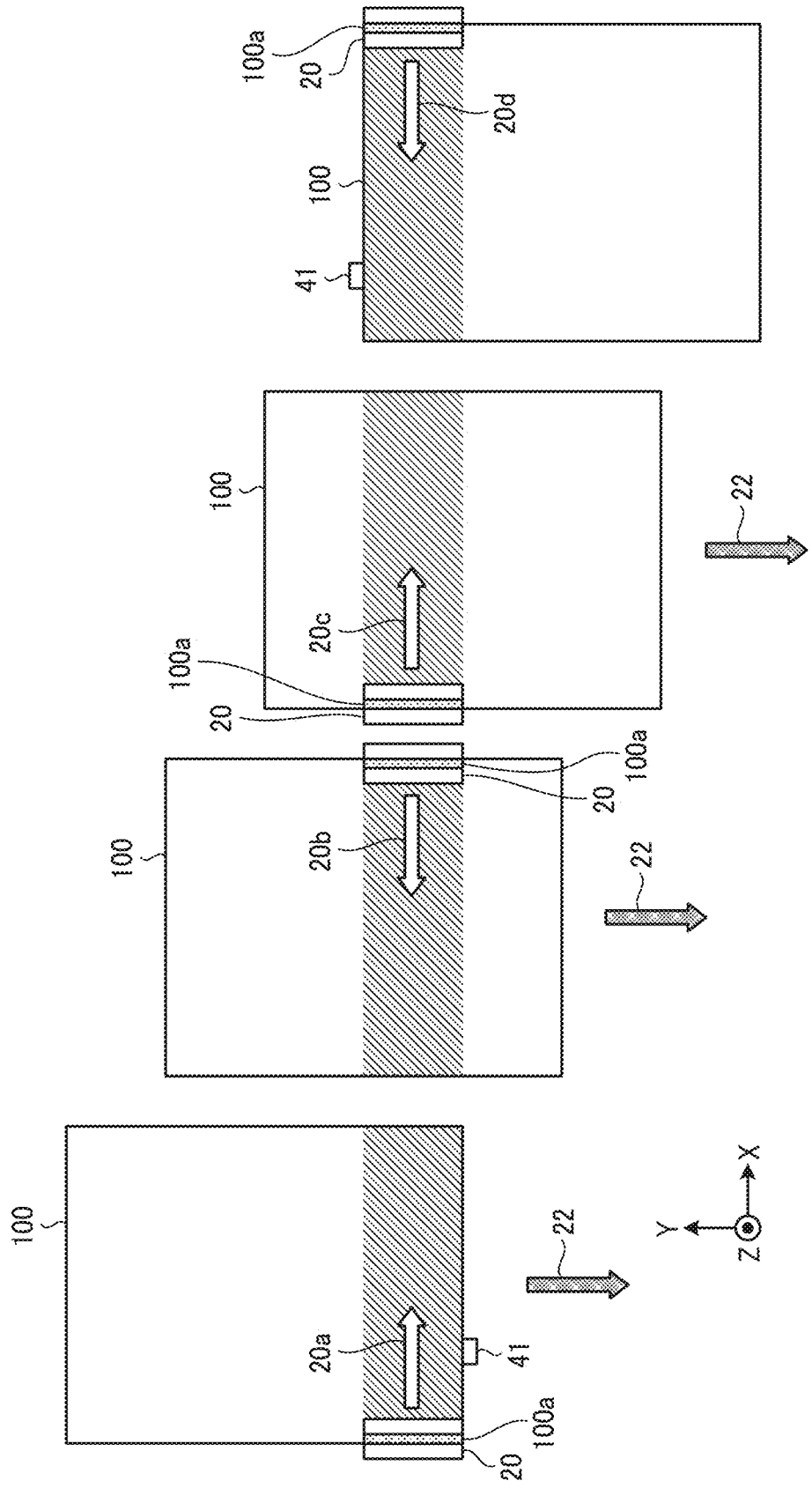
FIG. 10A, FIG. 10B, FIG. 10C, and FIG. 10D are plan views of a sheet as viewed in the +Z-axis direction when the color data of the sheet is being obtained in a spectral-characteristic acquisition apparatus, according to an embodiment of the present disclosure.

In FIG. 10A, the color data obtainer 20 is positioned at an end of the sheet 100 in the −X-axis direction and the −Y-axis direction. From the position illustrated in FIG. 10A, the color data obtainer 20 is continuously conveyed in a direction 20a indicated by a hollow arrow. Such continuous conveyance of the color data obtainer 20 may be referred to as a scan drive in the following description. While the color data obtainer 20 is continuously conveyed, the spectroscopic unit 80 obtains the color data of the color-data acquisition area 21 of the sheet 100 at predetermined time intervals. The predetermined time intervals are, for example, the frame periods of the imaging device 84. At that moment in time, the conveyance of the sheet 100 is stopped.

Once the spectroscopic unit 80 is conveyed to the end of the sheet 100 in the +X-axis direction, the conveyance of the color data obtainer 20 is stopped.

In the arrangement of the sheet 100 and the sheet sensor 41 as illustrated in FIG. 10A, it is detected that the sheet 100 is at the position where the color data is to be obtained, based on the output from the sheet sensor 41.

FIG. 10B illustrates the sheet 100 that is conveyed by a specified length in the +Y-axis direction from the position as illustrated in FIG. 10A.

The specified length is equivalent to, for example, the length in the Y-axis direction corresponding to the area from which the color data is to be obtained by the spectroscopic unit 80. In FIG. 10B, the color data obtainer 20 is positioned at an end of the sheet 100 in the +X-axis direction.

From the position illustrated in FIG. 10B, the color data obtainer 20 is continuously conveyed in a direction 20b indicated by a hollow arrow. While the color data obtainer 20 is continuously conveyed, the spectroscopic unit 80 obtains the color data of the color-data acquisition area 21 of the sheet 100 at predetermined time intervals. In a similar manner to the above, the conveyance of the sheet 100 is stopped at this time. Once the color data obtainer 20 is conveyed to the end of the sheet 100 in the −X-axis direction, the conveyance of the color data obtainer 20 is stopped.

Also in FIG. 10C and FIG. 10D, in a similar manner to the above, the color data obtainer 20 obtains the color data from the color-data acquisition area 21 of the sheet 100.

In the arrangement of the sheet 100 and the sheet sensor 41 as illustrated in FIG. 10D, it is detected that the sheet 100 has moved away from the position where the color data is to be obtained, based on the output from the sheet sensor 41.

Through the operations as illustrated in FIG. 10A, FIG. 10B, FIG. 10C, and FIG. 10D, the color data in the entirety of the sheet 100 can be obtained. In the above description, the color data obtainer 20 is conveyed four times in the X-axis direction to acquire the color data in the entirety of the sheet 100. However, no limitation is indicated thereby, and the number of times the sheet is to be conveyed may be any desired number determined based on the size of the sheet 100.

Figure 11:
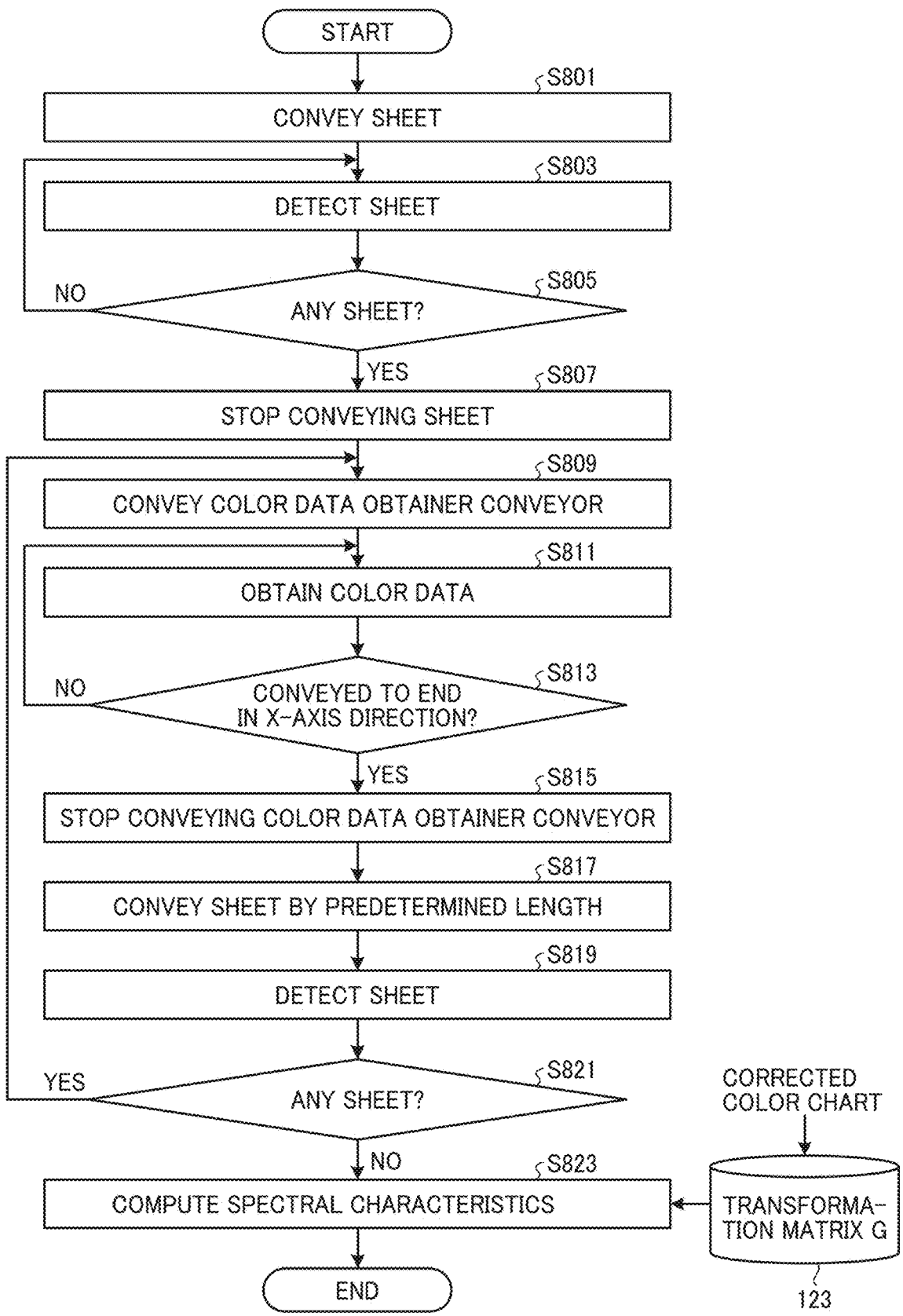
FIG. 11 is a flowchart of the acquisition processes of the spectral characteristics in a spectral-characteristic acquisition apparatus, according to an embodiment of the present disclosure.

FIG. 11 is a flowchart of the acquisition processes of the spectral characteristics in the spectral-characteristic acquisition apparatus 10, according to the present embodiment.

Firstly, in a step S801, the sheet conveyor 30, the sheet conveyor 31, and the sheet conveyor 32 convey the sheet 100 in the Y-axis direction.

Subsequently, in a step S803, the sheet sensor 41 obtains a detection signal that indicates whether the sheet 100 is at the position where the color data is to be obtained, and outputs the obtained detection signal to the controller 300.

Subsequently, in a step S805, the controller 300 determines whether the sheet 100 is at the position where the color data is to be obtained, based on the detection signal obtained by the sheet sensor 41.

Once it is determined in the step S805 that the sheet 100 is at the position where the color data is to be obtained, in a step S807, the sheet conveyor 30, the sheet conveyor 31, and the sheet conveyor 32 stop conveying the sheet 100 in the Y-axis direction. On the other hand, when it is determined that the sheet 100 is not at the position where the color data is to be obtained, the process returns to the step S803.

Subsequently, in a step S809, the color data obtainer conveyor 40 continuously conveys the color data obtainer 20 in the X-axis direction.

Subsequently, in a step S811, the color data obtainer 20 obtains the color data at predetermined time intervals. In other words, the imaging device 84 of the color data obtainer 20 captures a plurality of diffraction patterns A, B, and C formed by the light reflected from the color-data acquisition area 21, and outputs the captured diffraction patterns as color data.

Subsequently, in a step S813, the controller 300 determines whether the color data obtainer 20 has been conveyed to an end in the X-axis direction. In other words, it is determined whether the color data has been obtained in the entire range in the X-axis direction.

When it is determined in the step S813 that the color data obtainer 20 has been conveyed to the end in the X-axis direction, in a step S815, the color data obtainer conveyor 40 stops conveying the color data obtainer 20. When it is determined in the step S813 that the sheet has not been conveyed, the process returns to the step S811.

Subsequently, in a step S817, the sheet conveyor 30, the sheet conveyor 31, and the sheet conveyor 32 convey the sheet 100 by a predetermined length in the Y-axis direction.

Subsequently, in a step S819, the sheet sensor 41 obtains a detection signal that indicates whether the sheet 100 is at the position where the color data is to be obtained, and outputs the obtained detection signal to the controller 300.

Subsequently, in a step S821, the controller 300 determines whether the sheet 100 is at the position where the color data is to be obtained, based on the detection signal obtained by the sheet sensor 41.

When it is determined in the step S821 that the sheet 100 is at the position where the color data is to be obtained, the process returns to the step S809, and the color-data acquisition is continued. On the other hand, when it is determined in the step S821 that the sheet 100 is not at the position where the color data is to be obtained, in a step S823, the spectral-characteristic computing unit 113 uses the transformation matrix G stored in the transformation-matrix storage unit 123 to compute the spectral characteristics of the sheet 100 based on the obtained color data.

As a result, the acquisition processes of the spectral characteristics by the spectral-characteristic acquisition apparatus 10 according to the present embodiment are completed.

As described above, the spectral-characteristic acquisition apparatus 10 according to the present embodiment conveys the sheet 100, and can obtain the color data of the entirety of the sheet 100 while conveying the color data obtainer 20 having a plurality of spectral sensors in the width direction of the sheet 100.

The spectral-characteristic acquisition apparatus 10 according to the present embodiment has a function to correct the transformation matrix G, and such a function of the spectral-characteristic acquisition apparatus 10 is described below. In such correction, the color charts for correction 50 are used. The transformation matrix that is stored in the transformation-matrix storage unit 123 is corrected using the color data obtained from the color charts for correction 50 by the color data obtainer 20. The color charts for correction 50 according to the present embodiment serves as a plurality of color charts for correction that have a plurality of color chart whose spectral characteristics are known.

It is desired that the multiple color areas whose colors differ from one another in the color charts for correction 50 be evenly selected from, for example, the color range or the color gamut that can be reproduced on an image in the color space of, for example, an XYZ color system and a L*a*b* color system.

In a similar manner to the reference sample as described above, the preparation, maintenance, and measurement of such a color area in the color charts for correction 50 require a large amount of time and cost. For this reason, a small number of color areas tend to be used within a range in which the estimation accuracy of the spectral characteristics can be maintained to a sufficient degree. Typically, several colors to several tens of colors, which are selected from a color-reproducible range of image formation, are used. However, in order to enhance the estimation accuracy of the spectral characteristics and perform measurements with a high degree of precision, areas of several hundred to several thousand colors are used. This is typical when multicolor coloring materials of four or more colors are used in, for example, electrophotography and ink-jet printing for high resolution. The term multicolor as used herein refers to, for example, orange, green, white, clear, and fluorescent colors in addition to yellow, magenta (M), cyan (C), and black (K).

In the present embodiment, reference samples of several colors to several thousand colors selected from a color reproducible range of image formation by the image forming apparatus are used.

Figure 12:
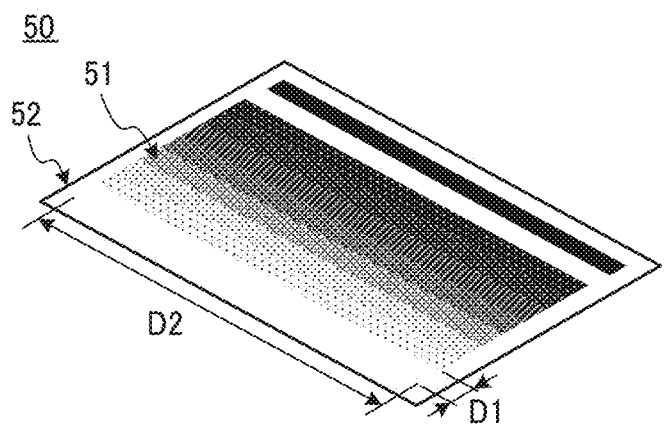
FIG. 12 is a diagram illustrating color charts for correction provided for a spectral-characteristic acquisition apparatus, according to an embodiment of the present disclosure.

FIG. 12 illustrates color charts for correction 50 that include such reference samples, according to the present embodiment.

In FIG. 12, the color charts for correction 50 include a plate-like component 52 formed by cutting a metal material such as aluminum, and a plurality of color charts 51 disposed on an upper surface of the plate-like component 52. The multiple color charts 51 is a band-like member colored with toned paint. The width D1 and the length D2 of each band are satisfactory as long as it is wider than a range in which the spectroscopic unit 80 can obtain color data at a time. For example, when the color-data obtaining ranges in the width direction and the conveyance direction are 1 mm and 100 mm, respectively, the width D1 of the band may be 1 mm or more, and the length D2 may be 100 mm or more. In the color chart for correction 50, the multiple color charts 51 as above are arranged in the width direction on the plate-like component 52 such that the length direction will approximately be parallel to the conveyance direction.

The multiple color charts 51 according to the present embodiment may be directly applied to and formed on the plate-like component 52. Alternatively, a band-like sheet on which a color image is formed may be adopted as the multiple color charts 51, and maybe pasted onto the plate-like component 52. The plate-like component 52 is made large enough not to touch the multiple color charts 51 when held or conveyed, and a plurality of plate-like components 52 are prepared when the number of colors of the multiple color charts 51 is large.

Figure 13:
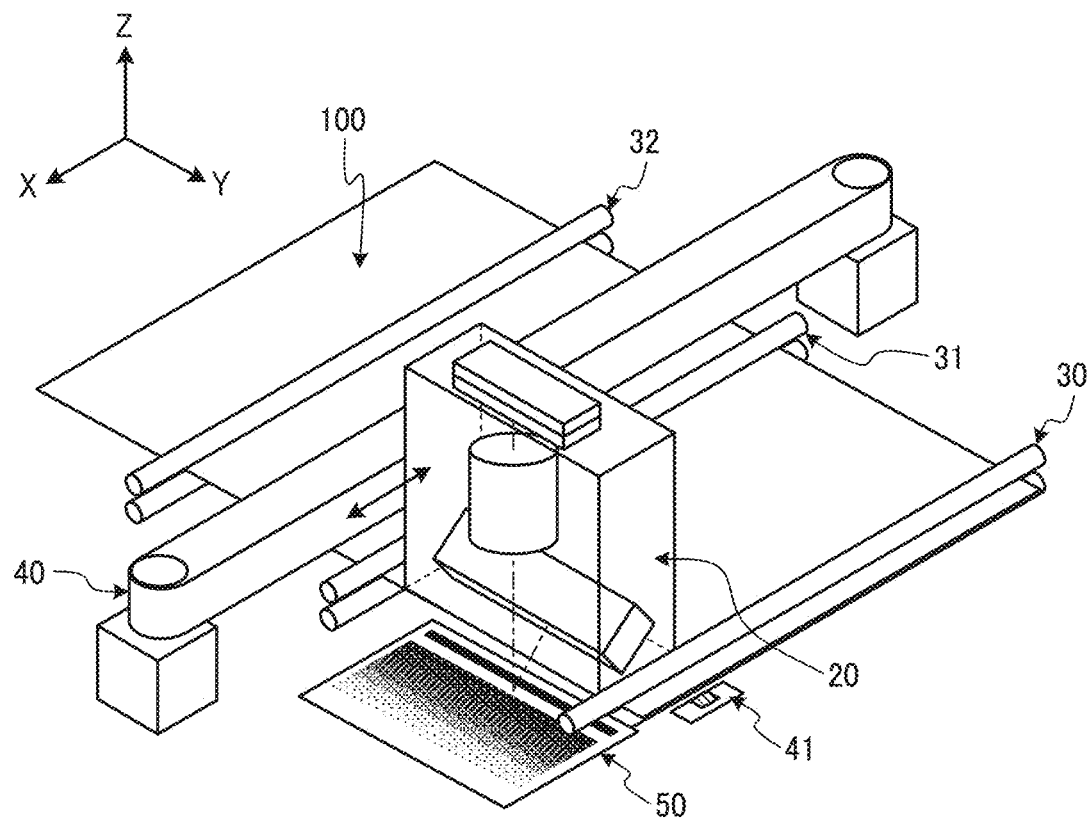
FIG. 13 is a perspective view of a spectral-characteristic acquisition apparatus, illustrating its arrangement when performing the correction, according to an embodiment of the present disclosure.

FIG. 13 is a perspective view of the spectral-characteristic acquisition apparatus 10, illustrating its arrangement when performing the correction, according to the present embodiment.

As illustrated in FIG. 13, the sheet 100 is placed within a range in which the color data obtainer 20 is conveyed, and the color charts for correction 50 are placed adjacent to the sheet 100 in the width direction. In other words, the color charts for correction 50 are arranged in an area other than the area in which the sheet 100 is to be placed within the range in which the color data obtainer 20 is conveyed by the color data obtainer conveyor 40. By conveying the color data obtainer 20 to the position of the color charts for correction 50, correction using the color charts for correction 50 can be performed.

The spectral characteristics of each one of the color charts that are included in the color charts for correction 50 are measured in advance using a high-accuracy spectrometer, and a matrix R1 that indicates the spectral characteristics of the object area is stored in advance in the reference-data storage unit 121.

A method of correcting the transformation matrix G using the transformation-matrix calculation unit 112 is described below. Each one of the spectral sensors provided for the color data obtainer 20 includes a transformation matrix G. The transformation matrix G of each one of the multiple spectral sensors is corrected by the transformation-matrix calculation unit 112. The transformation-matrix calculation unit 112 according to the present embodiment serves as a transformation matrix correction unit.

When the transformation matrix G is corrected, the color data obtainer 20 moves to the position of the color charts for correction 50. The color charts for correction 50 are irradiated with the light emitted from the linear light source 60, and each one of the multiple spectral sensors of the color data obtainer 20 captures diffraction patterns and outputs the color data.

Firstly, the transformation-matrix calculation unit 112 obtains a matrix Rref indicating the spectral characteristics of the reference sample measured in advance and the matrix R1 indicating the spectral characteristics of the multiple color charts 51 of the color charts for correction 50 from the reference-data storage unit 121, and obtains a matrix Rrev by adding the matrix R1 to the matrix Rref. The transformation-matrix calculation unit 112 obtains a matrix Vrev by adding the matrix V1 obtained from the multiple color charts 51 to the matrix Vref obtained from the reference sample stored in the color-data storage unit 122.

The transformation-matrix calculation unit 112 obtains the transformation matrix G1 based on the fifth equation using the matrix Rrev and the matrix Vrev obtained as above, and stores the corrected transformation matrix G1 in the transformation-matrix storage unit 123.

Figure 14:
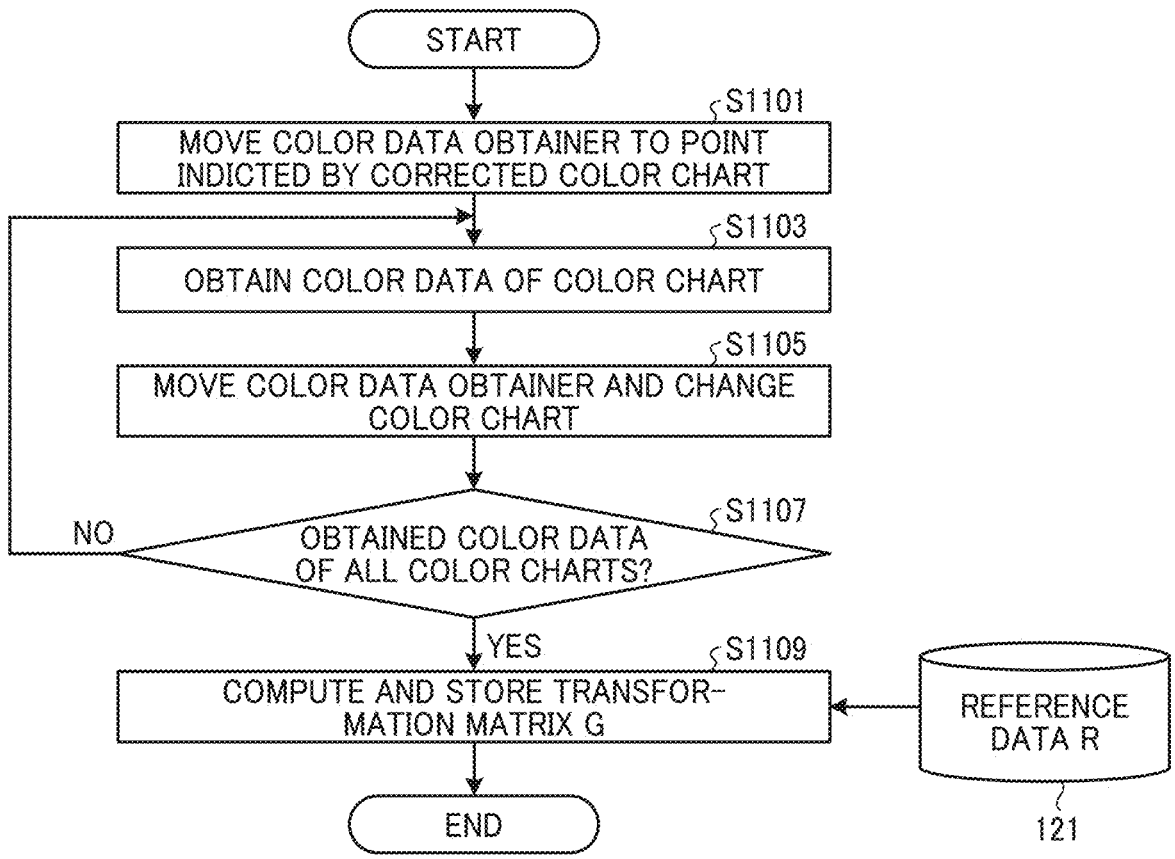
FIG. 14 is a flowchart of the correction processes of a transformation matrix by a spectral-characteristic acquisition apparatus, according to an embodiment of the present disclosure.

FIG. 14 is a flowchart of the correction processes of a transformation matrix by the spectral-characteristic acquisition apparatus as described above, according to the present embodiment.

Firstly, in a step S1101, the color data obtainer conveyor 40 conveys the color data obtainer 20 in the width direction of the sheet 100, and moves the color data obtainer 20 to the position of the color chart closest to the end in the color charts for corrections 50. The color chart closest to the end is, for example, as illustrated in FIG. 13, the color chart closest to the end of the color chart in the −X-axis direction.

Subsequently, in a step S1103, the color data obtainer 20 obtains the color data of the color chart.

Subsequently, in a step S1105, the color data obtainer conveyor 40 conveys the color data obtainer 20 in the width direction in order to change the color chart from which the color data is to be obtained.

Subsequently, in a step S1107, the controller 300 determines whether the color data of all the color charts have been obtained.

When it is determined in the step S1107 that the color data of all the color charts have been obtained, in a step S1109, the transformation-matrix calculation unit 112 obtains the transformation matrix G1 based on the fifth equation, and stores the corrected transformation matrix G1 in the transformation-matrix storage unit 123.

Figures 15, 16:
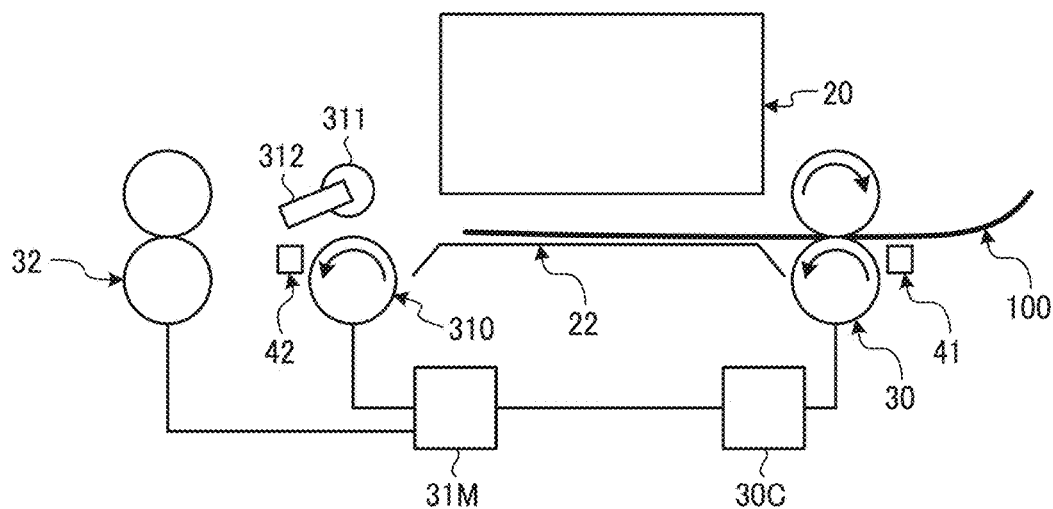
FIG. 15 is a diagram illustrating the spectral characteristics obtained for each color chart by a plurality of spectral sensors of a spectral-characteristic acquisition apparatus, according to an embodiment of the present disclosure.
FIG. 16 is a diagram illustrating a configuration or structure around a plurality of sheet conveyors of a spectral-characteristic acquisition apparatus, according to a second embodiment of the present disclosure.

FIG. 15 is a table of the spectral characteristics obtained for each one of the color charts by each one of a plurality of spectral sensors 80*m* in the color data obtainer 20, according to the present embodiment.

On the other hand, when it is determined in the step S1107 that not the color data of all the color charts have been obtained, the process returns to the step S1103, and the color data of the next color chart is obtained.

The transformation matrix G1 is corrected as described above. The spectral-characteristic computing unit 113 according to the present embodiment can use the corrected transformation matrix G1 to estimate the spectral characteristic of the sheet 100 with a high degree of precision.

As described above, according to the present embodiment, the color data obtainer 20 is conveyed in the width direction. Due to such a configuration, even when the width of the image formed on the sheet 100 is wide, the color data over the entire width of the image can be obtained without using an expensive light source that can irradiate the entire width of the image at once. Due to such a configuration, the spectral-characteristic acquisition apparatus 10 that can obtain the spectral characteristics with a high degree of precision can be implemented at a low cost with no need for an expensive light source.

As a plurality of spectral sensors are arrayed in the conveyance direction of the sheet 100, for example, the spectral characteristics of the sheet 100 in a wider range in the conveyance direction can be obtained at once. The conveyance of the color data obtainer 20 and the conveyance of the sheet 100 may be performed in a cooperative manner to obtain the spectral characteristics of a wide range of the sheet 100 at high speed.

On the other hand, by correcting the transformation matrix using the color charts for correction 50, the changes over time in the accuracy of the acquisition of the spectral characteristics due to, for example, the changes in outside air temperature or the characteristics of the wavelength of the light source can be controlled.

According to the present embodiment, the color charts for correction 50 may be arranged in an area other than the area in which the sheet 100 is disposed within the range in which the color data obtainer 20 is conveyed. Moving the color data obtainer 20 enables switching between a spectral-characteristic acquisition mode and a correction mode. Accordingly, correction can be easily performed without arranging a complicated configuration or mechanism used for mode switching. The color data obtainer conveyor 40 according to the present embodiment that moves the color data obtainer 20 to the position where the color charts for correction 50 are arranged serves as a mode switching unit.

The multiple color charts 51 are arranged such that the longer-side direction of the multiple color charts 51 having a band-like shape will be parallel to the conveyance direction of the sheet 100. According to such a configuration, the multiple spectral sensors of the color data obtainer 20 can be corrected at once, and correction can be efficiently performed.

As described above, according to the present embodiment, the sheet 100 can be stopped at a stop position in the measurable area in a stable manner. Moreover, according to the present embodiment, the load on the motor can be reduced by reducing the conveyance speed of the sheet in stages, and the motor can be instantaneously stopped in response to a turning-on signal of the sheet sensor 42. As a result, the sheet 100 can be stopped at a desired position.

Second Embodiment

A second embodiment of the present disclosure is described below.

The second embodiment of the present disclosure is different from the first embodiment of the present disclosure in that the sheet conveyor 30, the sheet conveyor 31, and the sheet conveyor 32 are coupled to the same drive motor 31M. Note that like reference signs are given to elements similar to those described in the first embodiment, and their detailed description is omitted in the description of the second embodiment of the present disclosure.

FIG. 16 is a diagram illustrating a configuration or structure around the sheet conveyor 30, the sheet conveyor 31, and the sheet conveyor 32 of the spectral-characteristic acquisition apparatus 10, according to the second embodiment of the present disclosure.

As illustrated in FIG. 16, the sheet conveyor 30, the sheet conveyor 31, and the sheet conveyor 32 are coupled to the same drive motor 31M. The sheet conveyor 30 is coupled to a clutch 30C that can turn on or turn off the transmission of the driving force of the sheet conveyor 31.

The conveyance of the sheet 100 in the Y-axis direction is described below.

Figure 17A:
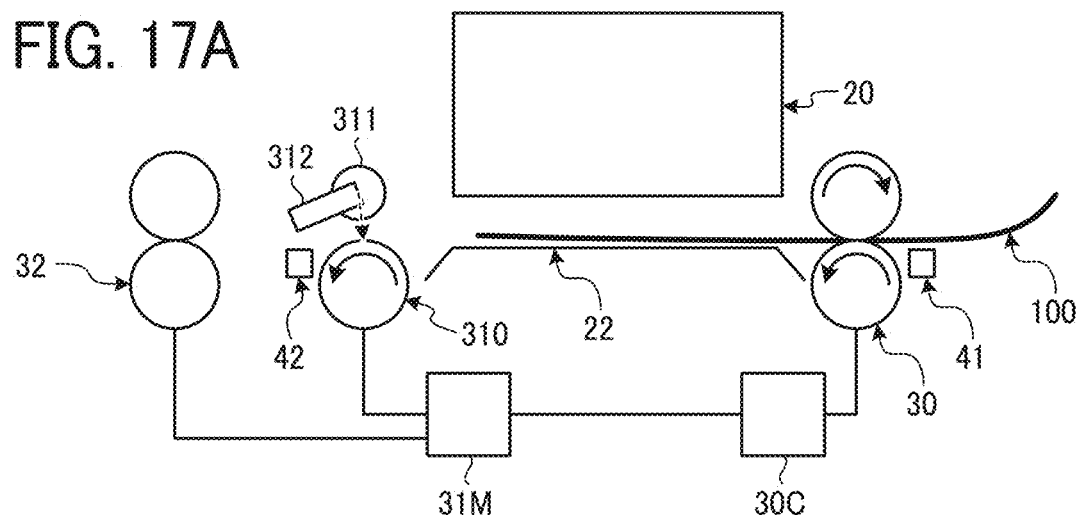
FIG. 17A, FIG. 17B, and FIG. 17C are schematic views of the operation of a plurality of sheet conveyors according to a second embodiment of the present disclosure.
Figure 17B:
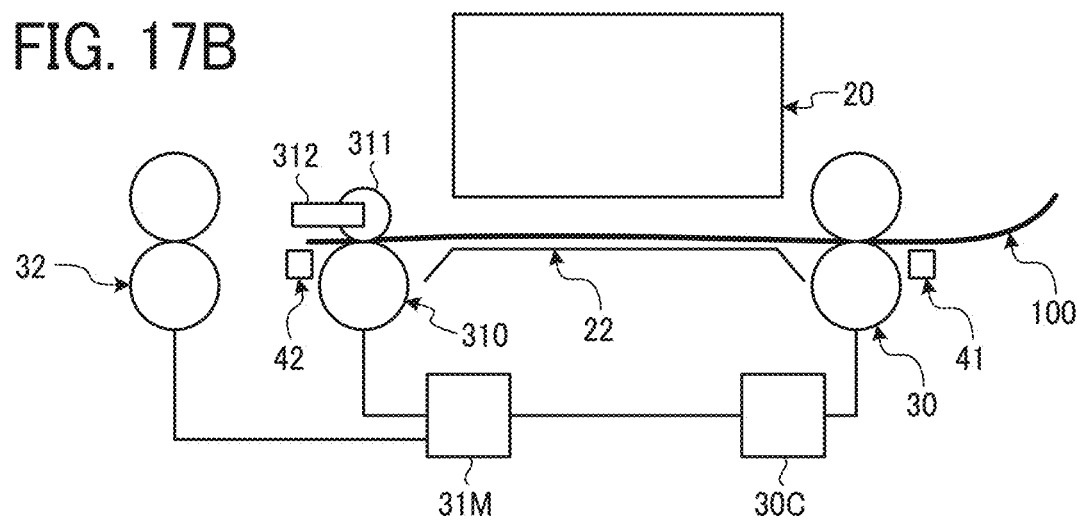
Figure 17C:
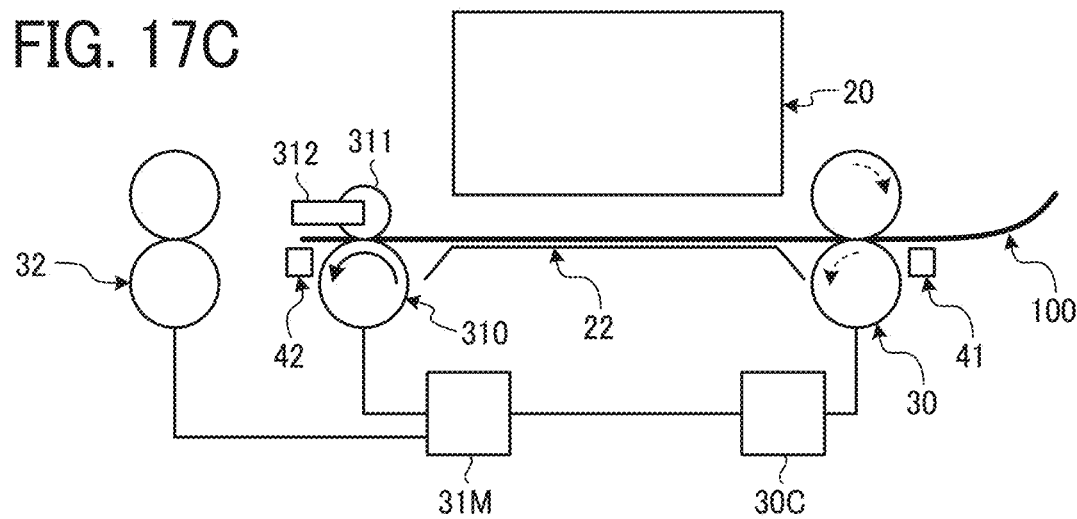

FIG. 17A, FIG. 17B, and FIG. 17C are schematic views of the operation of the sheet conveyor 30 and the sheet conveyor 31 according to the second embodiment of the present disclosure.

Firstly, the controller 300 turns on the drive motor 31M to convey the sheet 100 in the conveyance direction (see FIG. 17A). During such conveyance, the clutch 30C is turned on. In other words, the clutch 30C engages power transmission during such conveyance.

Subsequently, when the sheet sensor 42 detects the leading end of the sheet 100, the controller 300 turns off the drive motor 31M to stop the conveyance of the sheet 100, and drives the arm 312 to press the roller 311 against the sheet 100 (see FIG. 17B).

Subsequently, the controller 300 turns off the clutch 30C and disengages power transmission to operate the drive motor 31M by a predetermined amount in order to smooth out the slack or wrinkles of the sheet 100 (see FIG. 17C). As the roller 310 of the sheet conveyor 31 on the downstream portion of the color-data acquisition area 21 rotates by a predetermined amount, the sheet 100 is fed by a predetermined amount in the conveyance direction with the rotation of the driven roller 311. The driving force of the sheet conveyor 30 at an upstream portion of the color-data acquisition area 21 is 0. Accordingly, when the sheet conveyor 31 at a downstream portion of the color-data acquisition area 21 sends out the sheet 100 in the conveyance direction, the slack, sag, or wrinkles of the sheet 100 are smoothed out. After that, even if the sheet 100 is under tension due to the load and the degree of tension reaches a predetermined value, the sheet conveyor 30 on the upstream portion of the color-data acquisition area 21 rotates as pulled by the sheet 100, or the sheet 100 is pulled by the sheet conveyor 30 on the upstream portion of the color-data acquisition area 21 in the conveyance direction. Accordingly, the damage to the sheet 100 can be reduced.

In the present embodiment, the clutch 30C is turned on or turned off to engage or disengage the driving force of the drive motor 31M. However, no limitation is intended to the configuration or structure in which the clutch 30C is turned off to disengage the driving force of the drive motor 31M. An alternative configuration may be adopted in which the clutch 30C is turned off to switch the gear to a lighter gear. Even in such cases, the driving force of the sheet conveyor 31 on the downstream portion of the color-data acquisition area 21 is greater than that of the sheet conveyor 30 on an upstream portion of the color-data acquisition area 21. Accordingly, the slack and wrinkles of the sheet 100 can be smoothed out with minimized damage.

With such control, the sheet 100 can be conveyed to a stable position of the color-data acquisition area 21, and color measurement can stably be performed as there is no slack, sag, or wrinkle. Further, the damage to the sheet 100 can be further reduced.

As described above, according to the present embodiment, a spectral-characteristic acquisition apparatus provided with a plurality of arrayed spectral sensors can be implemented at a low cost. Moreover, according to the present embodiment, a spectral-characteristic acquisition apparatus that uses a plurality of spectral sensors to two-dimensionally scan a recording medium and that does not cause wrinkles or floatation of a recording medium even if the interval between a couple of pairs of rollers that hold a recording medium is long can be implemented at low cost.

In the above description, some preferred embodiments of the present disclosure and the modifications of those embodiments of the present disclosure are described. However, the description of the above embodiments and the modifications of those embodiments is given by way of example, and no limitation is intended thereby.

Note that numerous additional modifications and variations are possible in light of the above teachings. It is therefore to be understood that within the scope of the appended claims, the embodiments of the present disclosure may be practiced otherwise than as specifically described herein. For example, elements and/or features of different illustrative embodiments may be combined with each other and/or substituted for each other within the scope of this disclosure and appended claims.

Any one of the above-described operations may be performed in various other ways, for example, in an order different from the one described above.

Each of the functions of the described embodiments may be implemented by one or more processing circuits or circuitry. Processing circuitry includes a programmed processor, as a processor includes circuitry. A processing circuit also includes devices such as an application-specific integrated circuit (ASIC), digital signal processor (DSP), field-programmable gate array (FPGA), and conventional circuit components arranged to perform the recited functions.

What is claimed is:

1. A spectral-characteristic acquisition apparatus comprising:
a conveyor including
a first conveyance roller pair;
a second conveyance roller pair downstream from the first conveyance roller pair in a conveyance direction;
a sensor configured to detect that an object conveyed in the conveyance direction has reached the second conveyance roller pair;
a pressurizer configured to apply pressure to the object;
a color data obtainer configured to obtain color data from the object at a position where the object stops moving; and
circuitry configured to
cause the pressurizer to apply pressure to the object in response to the sensor detecting that the object has reached the second conveyance roller pair,
cause the second conveyance roller pair to drive with a driving force greater than a driving force of the first conveyance roller pair in response to the pressurizer applying pressure to the object, and
estimate a spectral characteristic of the object based on the color data obtained by the color data obtainer.

2. The spectral-characteristic acquisition apparatus according to claim 1, wherein the circuitry is further configured to cause the second roller pair to drive the object with the driving force greater than the driving force of the first conveyance roller pair, while the pressurizer is pressing the object.

3. The spectral-characteristic acquisition apparatus according to claim 1,
wherein the circuitry is configured to
turn off a driving force of the first conveyance roller pair in response to detecting that the object has reached the second conveyance roller pair by the sensor, and
turn on the driving force of the first conveyance roller pair in response to the second conveyance roller pair being driven by an amount.

4. The spectral-characteristic acquisition apparatus according to claim 1,
wherein the circuitry is configured to
disengage a clutch used to convey driving force to the first conveyance roller pair in response to detecting that the object has reached the second conveyance roller pair by the sensor, and
engage the clutch in response to the second conveyance roller pair being driven by an amount.

5. The spectral-characteristic acquisition apparatus according to claim 1, further comprising
a second conveyor configured to convey the color data obtainer in a direction intersecting with the conveyance direction.

6. The spectral-characteristic acquisition apparatus according to claim 1,
wherein the sensor is downstream from the second conveyance roller pair in the conveyance direction.

7. The spectral-characteristic acquisition apparatus according to claim 1,
wherein the conveyor is configured to convey the object at a first conveyance speed, and reduce conveyance speed of the object from the first conveyance speed to a second conveyance speed before the sensor detects that the object has reached the second conveyance roller pair.

8. The spectral-characteristic acquisition apparatus according to claim 1, wherein the second conveyance roller pair includes the pressurizer.

9. The spectral-characteristic acquisition apparatus according to claim 8, wherein the pressurizer includes an arm configured to cause a first roller of the second conveyance roller pair to press against a second roller of the second conveyance roller pair.

10. The spectral-characteristic acquisition apparatus according to claim 1, wherein the color data obtainer is configured to obtain the color data from the object in response to the second conveyance roller pair driving an amount with the pressurize applying pressure.

11. The spectral-characteristic acquisition apparatus according to claim 1, wherein the first conveyance roller pair is configured to rotate by being pulled by the object when the second conveyance roller pair drives the driving force greater than the first conveyance roller pair.

12. The spectral-characteristic acquisition apparatus according to claim 1, wherein the circuitry is configured to cause the first conveyance roller pair and the second conveyance roller pair to stop conveying the object in response to the sensor detecting that the object has reached the second conveyance roller pair.

13. The spectral-characteristic acquisition apparatus according to claim 12, wherein the circuitry is configured to cause the pressurizer to apply pressure to the object in response to the object stopping in the conveyance direction.

14. A method of acquiring a spectral characteristic, the method comprising:
conveying an object in a conveyance direction from a first conveyance roller pair to a second conveyance roller pair downstream from the first conveyance roller pair in the conveyance direction;
detecting that the object has reached the second conveyance roller pair;
applying pressure, via a pressurizer, to the object in response to detecting that the object has reached the second conveyance roller pair;
driving the second conveyance roller pair with a driving force greater than a driving force of the first conveyance roller pair in response to the pressurizer applying pressure to the object;
obtaining color data from the object at a position where the object is stopped; and
estimating a spectral characteristic of the object based on the color data.

15. The method of claim 14, wherein the second conveyance roller pair includes the pressurizer.

16. The method of claim 15, wherein the pressurizer includes an arm configured to cause a first roller of the second conveyance roller pair to press against a second roller of the second conveyance roller pair.

17. The method of claim 14, wherein the obtaining the color data from the object includes obtaining the color data from the object in response to the second conveyance roller pair driving an amount with the pressurizer applying pressure.

18. The method of claim 14, wherein the first conveyance roller pair is configured to rotate by being pulled by the object when the second conveyance roller pair drives the driving force greater than the first conveyance roller pair.

19. The method of claim 14, further comprising:
stopping conveyance of the object in response to detecting that the object has reached the second conveyance roller pair.

20. The method of claim 19, wherein the applying pressure includes applying the pressure in response to the stopping the conveyance of the object.

* * * * *